United States Patent
Judd et al.

(10) Patent No.: US 11,420,989 B2
(45) Date of Patent: Aug. 23, 2022

(54) CROSS-LINKABLE ORGANOMETALLIC LIGHT EMITTING LIGANDS AND COMPLEXES

(71) Applicant: LOMOX LIMITED, Congleton (GB)

(72) Inventors: Luke Judd, Congleton (GB); Matthew Aldred, Congleton (GB); Gene C. Koch, Congleton (GB)

(73) Assignee: LOMOX LIMITED, Congleton (GB)

( * ) Notice: Subject to any disclaimer, the term of this patent is extended or adjusted under 35 U.S.C. 154(b) by 455 days.

(21) Appl. No.: 16/490,146

(22) PCT Filed: Feb. 28, 2018

(86) PCT No.: PCT/GB2018/050519
§ 371 (c)(1),
(2) Date: Aug. 30, 2019

(87) PCT Pub. No.: WO2018/162880
PCT Pub. Date: Sep. 13, 2018

(65) Prior Publication Data
US 2020/0010495 A1    Jan. 9, 2020

(30) Foreign Application Priority Data
Mar. 6, 2017  (GB) ................... 1703525

(51) Int. Cl.
*C07F 15/00* (2006.01)
*C07F 7/08* (2006.01)
*H01L 51/00* (2006.01)
*H01L 51/50* (2006.01)

(52) U.S. Cl.
CPC .......... *C07F 15/004* (2013.01); *C07F 7/0816* (2013.01); *C07F 15/0086* (2013.01); *H01L 51/0003* (2013.01); *H01L 51/0012* (2013.01); *H01L 51/0015* (2013.01); *H01L 51/0035* (2013.01); *H01L 51/0043* (2013.01); *H01L 51/0085* (2013.01); *H01L 51/0087* (2013.01); *H01L 51/5016* (2013.01)

(58) Field of Classification Search
None
See application file for complete search history.

(56) References Cited

U.S. PATENT DOCUMENTS

2011/0089411 A1*  4/2011  Xia ............. H01L 51/506
                                                            564/8

FOREIGN PATENT DOCUMENTS

| CN | 101538289 A | 9/2009 |
|---|---|---|
| CN | 102558417 A | 7/2012 |
| JP | 2014-208642 A | 11/2014 |
| WO | 2005014723 | 2/2005 |
| WO | 2009022594 A1 | 2/2009 |
| WO | 2009158069 A1 | 12/2009 |
| WO | 2013004989 | 1/2013 |
| WO | 2016101573 A1 | 6/2016 |

OTHER PUBLICATIONS

Dainton F. S. et al., "The Heats of Polymerization of Some Cyclic and Ethylenic Compounds", Trans. Faraday Soc. 1960, 56, 1784-1792.
International Search Report and Written Opinion, PCT/GB2018/050519, dated May 2, 2018, 16 pages.
Great Britain Search Report, Application No. 1703525.4, dated Jan. 10, 2018, 1 page.
Neve et al., "Ionic luminescent cyclometalated Ir(III) complexes with polypyridine co-ligands," Inorganica Chimica Acta 2006, 359, pp. 1666-1672.
Diez et al., "Polarised phosphorescent emission in an organoplatinum(II)-based liquid-crystalline polymer," Chem. Commun., 2012, 48, pp. 10298-10300.
Aldred et al., "Organic electroluminescence using polymer networks from smectic liquid crystals," Liquid Crystals, vol. 33. No. 4, 2006, pp. 459-467.
Aldred et al., "Synthesis and mesomorphic behaviour of novel light-emitting liquid crystals," Liquid Crystals, vol. 32. No. 10, 2005, pp. 1251-1264.

(Continued)

*Primary Examiner* — Shane Fang
(74) *Attorney, Agent, or Firm* — Stinson LLP

(57) ABSTRACT

A 1, 4 bidentate ligand comprising first and second ligand centres,
wherein the first ligand centre is an $sp^2$-hybridised carbon or a nitrogen atom;
wherein the second ligand centre is a nitrogen atom in a five- or six-membered aromatic or hetero-aromatic ring, said ring having a substantially linear substituent $T^1$ meta or para to the nitrogen atom;
wherein $T^1$ has the formula 1:

$$-Ar^1{}_a-Y^1{}_b-Ar^2-[Y^2{}_c-Ar^2]_d-S-B \qquad (1)$$

and wherein $T^1$ is attached to the ring by $X^1$, wherein $X^1$ is a bond, a methylene group, a substituted methylene group, an oxygen atom or a sulphur atom,
wherein each $Ar^1$ and $Ar^2$ are independently selected from the group of $C_6$ to $C_{20}$ aromatic and $C_4$ to $C_{20}$ heteroaromatic groups,
wherein $Y^1$ and each $Y^2$ is independently an optionally substituted $C_2$ or acetonitrile trans double-bond linking moiety,
wherein a is 0, 1, 2 or 3,
wherein b is 0, 1 or 2,
wherein each c is independently 0, 1 or 2,
wherein d is 0, 1, 2, 3 or 4,
S is a flexible spacer, and
B represents a moiety having one or more cross-linkable functionalities. Network polymers, complexes, compositions, and devices based on this ligand. Method for forming devices based on this ligand.

20 Claims, 1 Drawing Sheet

(56) References Cited

OTHER PUBLICATIONS

Bloom et al., "Tervalent Conducting Polymers with Tailor-Made Work Functions: Preparation, Characterization, and Applications as Cathodes in Electroluminescent Devices," J. Am. Chem. Soc. 2001, vol. 123, No. 38, pp. 9436-9442.

Rodriguez-Redondo et al., "Red-light-emitting electrochemical cell using a polypyridyl iridium(III) polymer," Dalton Transactions, No. 44, Jan. 1, 2009, pp. 9787-9793.

Garelli et al., "Synthesis and characterization of amphiphilic platinum and palladium complexes linked to perfluoroalkylated sidechain disubstituted bipyridines," Inorganica Chimica Acta, vol. 194, Issue 2, Apr. 15, 1992, pp. 247-253.

Yeon Taik Kim et al., "Scanning tunneling microscopy studies of gold(111) derivatized with organothiols," J. Phys. Chem., 1992, 96 (18), pp. 7416-7421.

Arduini et al., "Communication between Components in Metal-Directed Assemblies of Oriented Calix[6]arene-Based Pseudorotaxanes and Rotaxanes," European Journal of Organic Chemistry, 2012, No. 5, pp. 1033-1038.

Kato et al., "Dichloro(4,4'-dinonyl-2,2'-bipyridine-k2N,N')platinum(II)," Acta Crystallographica Section C Crystal Structure Communications, C59, Feb. 2003, pp. m25-m26.

Jeum-Jong Kim et al., "A New Class of Cyclometalated Ruthenium Sensitizers of the Type $\hat{C}\hat{N}N$ for Efficient Dye-Sensitized Solar Cells," Inorganic Chemistry, 2011, vol. 50, No. 22, pp. 11340-11347.

Hagemann et al., "Synthesis of an All-in-One Molecule (for Organic Solar Cells)," J. Org. Chem., 2006, vol. 71, pp. 5546-5559.

"Ethylenic—Wiktionary", Wiktionary, Mar. 15, 2019, URL:https://en.wiktionary.org/wiki/ethylenic.

"Ethylene—Wiktionary", Wiktionary, Sep. 29, 2020, URL:https://en.wiktionary.org/wiki/ethylene.

Moss G. P. et al., "Glossary of class names of organic compounds and reactive intermediates based on structure (IUPAC Recommendations 1995)" Pure & Appl. Chem. vol. 67, Nos. 8/9, 1995, 1307-1375.

IUPAC: "Rules for Name Construction—IUPAC—Provisional Recommendations", IUPAC—Provisional Recommendations, 2004, 1-1306, URL:https://old.iupac.org/reports/provisional/abstract04/BB-prs310305/CompleteDraft.pdf.

Viau et al., "Synthesis of star-shaped metallo-polymeric chromophores by atom transfer radical polymerization," C. R. Chimie 8, 2005, pp. 1298-1307.

Constable et al., "Metallomacrocycles with a Difference: Macrocyclic Complexes with Exocyclic Ruthenium(II)-Containing Domains," Chem. Eur. J. 2009, 15, pp. 11746-11757.

Opris et al., "Shape-Persistent Macrocycles with Bipyridine Units: Progress in Accessibility and Widening of Applicability," Eur. J. Org. Chem., 2005, pp. 822-837.

Constable et al., "Diversification of ligand families through ferroin-neocuproin metal-binding domain manipulation," Dalton Trans., 2009, pp. 4918-4927.

Balasubramanian et al., "Langmuir-Schaefer Films of Distyrylphenanthrolines and Rhenium Tricarbonyl Chloride Complexes: Headgroup Influence on Anisotropy," Langmuir 1996, 12, pp. 4882-4888.

\* cited by examiner

CROSS-LINKABLE ORGANOMETALLIC LIGHT EMITTING LIGANDS AND COMPLEXES

REFERENCE TO RELATED APPLICATIONS

This application is a US national stage application based on PCT/GB2018/050519 filed Feb. 28, 2018 claiming priority to Great Britain application no. 1703525.4, filed Mar. 6, 2017, the entire disclosures of which are incorporated herein by reference.

FIELD OF THE INVENTION

This invention relates to cross-linkable ligands and, for example, octahedral bis-heteroleptic and tris-heteroleptic cross-linkable light emitting transition metal complexes of the formula $L^1L^2MA$ comprising said ligands, and in particular iridium (Ill), platinum (II), ruthenium (II) and osmium (II) complexes and their use as phosphorescent emitters in organic light emitting diode (OLED) devices.

BACKGROUND

Organic light emitting diodes (OLEDs) are light emitting diodes containing an emissive electroluminescent material comprising a film of organic material. The emissive organic layer of an OLED is usually sandwiched between two electrical contact layers. When a suitable voltage is applied across the diode light is emitted. For enhanced efficiency, in addition to the emissive layer, also referred to as the light emitting layer, an OLED device may also incorporate layers of charge transporting material located between the emissive layer and the electrical contact layers. These charge transporting layers may comprise either hole or electron transporting materials and these serve to facilitate the migration of charge-carrying holes and electrons through the device into the emissive layer, wherein they can combine to form a bound state called an exciton. The electrons in the exciton can, in due course, relax into a lower energy state by emitting radiation that, for an OLED device, is of a frequency most often in the visible region.

There is considerable ongoing interest in the development of new materials with improved properties that are suitable for use in the fabrication of OLED devices. Materials that, for example, function as emitters, are of particular interest. Many materials have been developed over the years in the attempt to produce improved OLED devices and in particular devices with optimal light output, energy efficiency and life time. Among these materials a particularly notable class is a family of organometallic materials, for example octahedral iridium (III) complexes, that can serve as phosphorescent light emitters in OLEDs. Octahedral iridium (III) complexes with two identical bidentate carbon nitrogen ligands and either a pair of ancillary ligands or a single bidentate auxiliary ligand have proven to be of particular interest, and have found widespread applications as phosphorescent light emitters. Organometallic emitters are particularly efficient because their available f-orbitals permit emission pathways that are unavailable to pure organic light emitters. The metal-to-ligand charge transfer (MLCT) properties of such complexes are described in Wilde at al J. Phys. Chem. 1991, 95. 629-634. Further examples of such compounds are described in Thompson et al, U.S. Pat. No. 6,830,828.

Notwithstanding their high emission efficiency, the practical application of prior art organometallic emitters is not without issue. For example, because the emitter complexes in the conventional OLED devices are oriented isotropically, i.e. the emitter complexes are randomly oriented, they emit light in an isotropic manner, i.e. in all directions. As a consequence of isotropic orientation of the emitters only a fraction of the light they emit is output from the device. The residual light energy, which is a substantial proportion, is absorbed internally by the materials that form the device. Therefore, there is a limit to the efficiency of the current OLED devices that incorporate the materials that form the state-of-the-art.

Chemistry of Material, 2013, 25, 2352-2358 discloses functionalisation of phenyl pyridine ligands to produce iridium complexes with improved solubility relative to conventional bis[4,6-(difluorophenyl)-pyridinato-N,C complexes.

Dalton Trans., 2011, 40, 12765 discloses one-photon photophysics and two-photon absorption spectra of several functionalised phenyl pyridine iridium complexes. In particular Dalton Trans., 2011, 40, 12765 discloses the two-photon absorption spectra of Ir(4-pe-2-ppy)$_2$(acac) shown below.

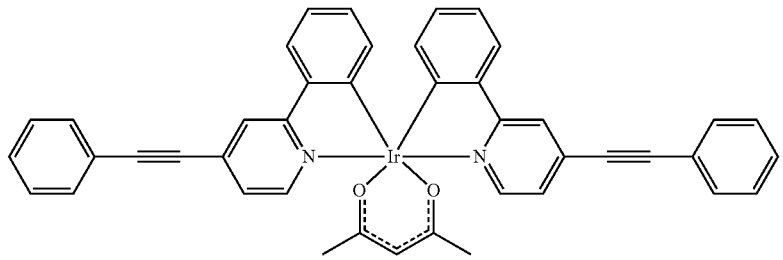

Dalton Trans., 2016, 45, 11496-11507 discloses the use of organolithium reagents for synthesising 4-aryl-2-phenylpyridines and their corresponding iridium complexes. Complexes containing 4-aryl-2-phenylpyridine ligands represent some of the most common versatile small-molecule emitters used in OLEDs. Dalton Trans., 2016, 45, 11496-11507 teaches a versatile synthetic route for the production of said ligands.

It would therefore be highly desirable to produce materials that emit light in a non-random, anisotropic, manner. It is an object of the present invention to provide new emitter materials that are capable of emitting light in a directionally oriented, or anisotropic manner. In some examples the materials of the present invention are capable of aligning with neighbouring materials in the emitter layer, for example liquid crystalline materials, that have intrinsically high degrees of structural order, thereby providing emissive layers with high structural order that as a result emit light in an anisotropic manner.

In addition, a further notable object of the present invention is the provision of materials that can be processed in simpler ways than current organometallic emitters. Presently, organometallic emitter species are often deposited as vapours under low pressure conditions. The materials of the present invention can be deposited in a controlled manner from solution in common solvents, such as organic solvents, to form a film when the solvent is evaporated, for example under reduced pressure, and can then be fixed in place by cross-linking, for example by exposing the resultant film to radiation, for example UV radiation. The resultant film is insoluble and can then be coated with further functional layers using the same solution deposition, evaporation and cross-linking approach. It is an object of the present invention therefore to provide materials that allow a simplification of the device fabrication process. Simplification of the fabrication process can enable new device architectures and reduce the cost of goods. Notably, solution-based processing as it allows patterned devices to be formed by the steps of masking/exposing to radiation, then washing off non-cross-linked materials. The materials of the present invention therefore possess a set of properties that render them highly valuable for the fabrication of OLED devices and other electronic devices.

Inorganica Chimica Acta, Vol. 359(5), 2006, (Neve, Francesco et al), pages 1666-1672, ISSN: 0020-1693, discloses ligands and iridium complexes.

Chemical Communications, Vol. 48(83), 2012, (Diez, Alvaro et al), pages 10298-10300, ISSN: 1359-7345 discloses platinum complexes.

CN 102558417 A discloses ligand structures.

Liquid Crystals, Vol. 33(4), 2006, (Aldred, Matthew et al), pages 459-467, ISSN: 0267-8292, discloses ligand structures.

Liquid Crystals, Vol. 32(10), 2005, (Aldred, Matthew P. et al), pages 1251-1264, ISSN: 0267-8292, discloses ligand structures.

Accordingly, it is desirable to provide an improved ligand for forming a complex for use in an OLED and/or to tackle at least some of the problems associated with the prior art or, at least, to provide a commercially viable alternative thereto.

SUMMARY OF THE INVENTION

In a first aspect the invention provides a 1, 4 bidentate ligand comprising first and second ligand centres,
wherein the first ligand centre is an sp2-hybridised carbon or a nitrogen atom;
wherein the second ligand centre is a nitrogen atom in a five- or six-membered aromatic or hetero-aromatic ring, said ring having a substantially linear substituent $T^1$ meta or para to the nitrogen atom;
wherein $T^1$ has the formula 1:

$$—Ar^1{}_a—Y^1{}_b—Ar^2—[Y^2{}_c—Ar^2]_d—S—B \quad (1)$$

and wherein $T^1$ is attached to the ring by $X^1$, wherein $X^1$ is a bond, a methylene group, a substituted methylene group, an oxygen atom or a sulphur atom,
wherein each $Ar^1$ and $Ar^2$ are independently selected from the group of $C_6$ to $C_{20}$ aromatic and $C_4$ to $C_{20}$ heteroaromatic groups,
wherein $Y^1$ and each $Y^2$ is independently an optionally substituted $C_2$ trans double-bond linking moeity, wherein a is 0, 1, 2 or 3,
wherein b is 0, 1 or 2,
wherein each c is independently 0, 1 or 2,
wherein d is 0, 1, 2, 3 or 4,
S is a flexible spacer, and
B represents a moiety having one or more cross-linkable functionalities.

The present invention will now be further described. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The present invention relates to a 1,4-bidentate ligand comprising first and second ligand centres. A ligand centre is the atom of a ligand that chemically binds to a metal atom in a complex.

The first ligand centre is an sp²-hybridised carbon or a nitrogen atom. An sp²-hybridised carbon or nitrogen ligand centre is a carbon or nitrogen atom that is covalently double bonded to an adjacent atom in the ligand and that forms a chemical bond to a metal atom in the overall organometallic complex. Preferably the first ligand centre is in a six-membered aromatic- or hetero-aromatic ring. Preferably the first ligand centre is a sp² hybridised carbon. Preferably the first ligand centre is benzene or pyridine.

The second ligand centre is a nitrogen atom in a five- or six-membered aromatic or hetero-aromatic ring. Examples of suitable rings include pyridine and pyrrole, as well as diazines and azoles, and oxygen or sulphur substituted analogues. The most preferred is pyridine.

The ring including the second ligand centre has a substantially linear substituent $T^1$ meta or para to the nitrogen atom. In the present application the terms ipso, ortho, meta and para are used to designate the relative position of substituents on 5 and 6 membered rings as shown below, relative to the ligand centre denoted D in the figures below.

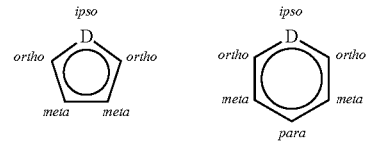

In the present application the term substantially linear is used to denote a series of moieties where the connections between moieties are in the para position or close thereto. Examples of close to para connections are:

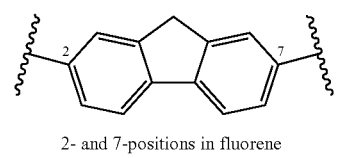

2- and 7-positions in fluorene

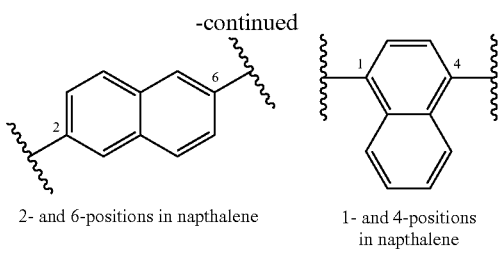

2- and 6-positions in napthalene 1- and 4-positions in napthalene

Preferred ligands are based on 2-phenylpyridine ring structures, where the nitrogen is one of the ligand centres, or 2,2-bipyridine ring structures, where both nitrogens are ligand centres. Fluorine substituted analogues of these structures may be useful in blue-shifting the emission. In particular the following structures are preferred.

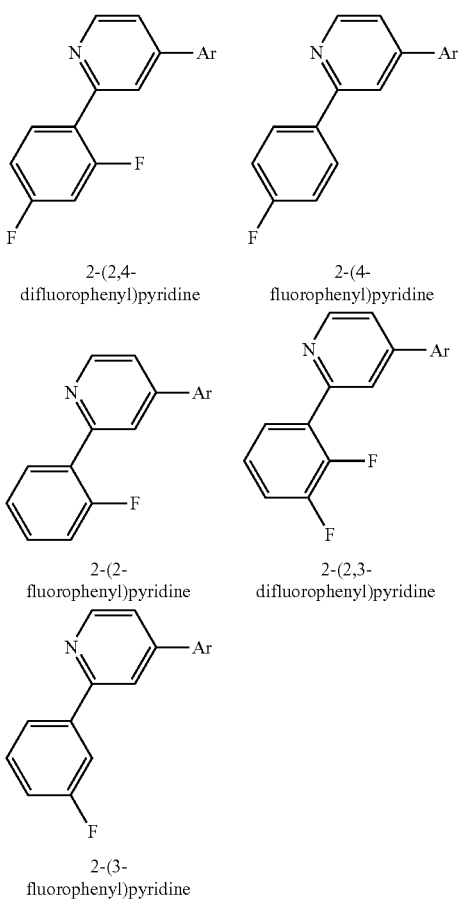

Ar shows the preferred position of the linear chain of structure (1) if only one such chain of structure (1) is present. $T^1$ has the formula 1:

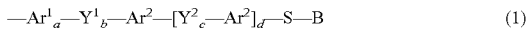

$—Ar^1{}_a—Y^1{}_b—Ar^2—[Y^2{}_c—Ar^2]_d—S—B$     (1)

$T^1$ is attached to the ring by $X^1$, wherein $X^1$ is a bond, a methylene group, a substituted methylene group, an oxygen atom or a sulphur atom. Preferably $X^1$ is a bond, since this helps to ensure that the linear form is maintained.

Each $Ar^1$ and $Ar^2$ are independently selected from the group of optionally substituted $C_6$ to $C_{20}$ aromatic and $C_4$ to $C_{20}$ heteroaromatic groups. Preferably each $Ar^1$ and $Ar^2$ are optionally substituted aromatic diradicals independently selected from the group consisting of 1,4-phenylene, naphthalene-1,4-diyl, naphthalene-2,6-diyl, perylene-3,10-diyl, pyrene-2,7-diyl, fluorene-2,7-diyl, fluorene-3,6-diyl, 9,9-dialkylfluorene-2,7-diyl, 9,9-dialkylfluorene-3,6-diyl, 9-(1'-alkylidene)fluorene-2,7-diyl, 2,5-dialkoxybenzene-1,4-diyl, m-xylene, p-xylene, durene and/or optionally substituted heteroaromatic diradicals independently selected from the group consisting of benzo[1,2-b:4,5-b']bis[1]benzothiophene-3,9-diyl, dibenzothiophene-3,7-diyl, [1]benzothieno[3,2-b][1]benzothiophene-2,7-diyl, 1,3,4-oxadiazole-2,5-diyl, 1,3,4-thiadiazole-2,5-diyl, 2,1,3-benzothiadiazole-4,7-diyl, 2,2'-dithiophene-5,5'-diyl, 4,7-dithien-2-yl-2,1,3-benzothiazole-5',5"-diyl, 4-alkyl-1,2,4-triazole-3,5-diyl, 4-thien-2-yl-2,1,3-benzothiazole-7,5'-diyl, 5,5-dioxodibenzothiophene-3,7-diyl, 5,11-dialkylindolo[3,2-b]carbazole-3,9-diyl, 5,11-dihydroindolo[3,2-b]carbazole-2,8-diyl, 9-alkylcarbazole-2,7-diyl, 9-alkylcarbazole-3,6-diyl, benzo[1,2-b:4,5-b']dithiophene-2,6-diyl, benzo[1,2-b:5,4-b']dithiophene-2,6-diyl, benzo[1,2-d:4,5-d']bisoxazole-2,6-diyl, benzo[1,2-d:5,4-d']bisoxazole-2,6-diyl, dithieno[3,2-b:2',3'-d]thiophene-2,6-diyl, imidazo[4,5-d]imidazole-2,5-diyl, oxazole-2,5-diyl, oxazolo[4,5-d]oxazole-2,5-diyl, oxazolo[5,4-d]oxazole-2,5-diyl, pyridine-2,5-diyl, pyrimidine-2,5-diyl, 5,5-dialkyl-5H-dibenzo[b,d]silole, pyridine-2,5-diyl, pyrimidine-2,5-diyl, thiazolo[4,5-d]oxazole-2,5-diyl, thiazolo[4,5-d]thiazole-2,5-diyl, thiazolo[5,4-d]oxazole-2,5-diyl, thiazolo[5,4-d]thiazole-2,5-diyl, thieno[3,2-b]thiophene-2,5-diyl, thiophene-2,5-diyl, furan-2,5-diyl and 1,2,4,5-tetrazine-3,6-diyl.

The most preferred embodiments of $Ar^1$ and/or $Ar^2$ groups are shown as Ar in the figure below:

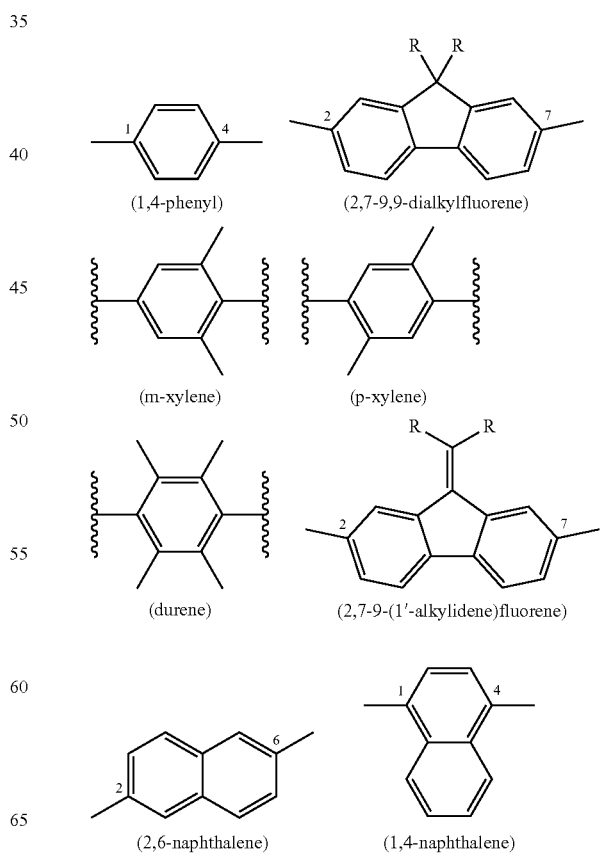

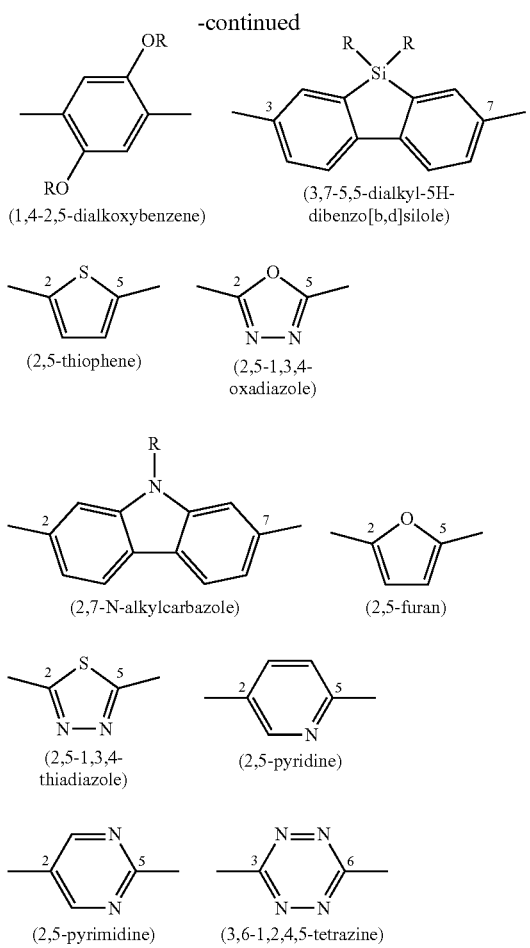

(1,4-2,5-dialkoxybenzene)
(3,7-5,5-dialkyl-5H-dibenzo[b,d]silole)
(2,5-thiophene)
(2,5-1,3,4-oxadiazole)
(2,7-N-alkylcarbazole)
(2,5-furan)
(2,5-1,3,4-thiadiazole)
(2,5-pyridine)
(2,5-pyrimidine)
(3,6-1,2,4,5-tetrazine)

The final $Ar^2$ group in the structure of formula (1) may preferably be a phenyl group. Such structures may be particularly preferred due to the ease of synthesis.

In some embodiments $Ar^1$ and $Ar^2$ are substituted with one or more alkyl or alkoxy groups. Substitution of the aromatic and/or heteroaromatic groups to include alkyl or alkoxy groups may improve the ligand solubility. Additionally, substitution of the aromatic and heteroaromatic groups may, advantageously, lead to twisting of the conjugated portion of the ligand. That is, steric clash between substituents on adjacent $Ar^1$ and/or $Ar^2$ groups may lead to twisting of the rings, increasing the dihedral angle between the planes of adjacent ring structures. Such twists in the conjugated portion of the molecule may be used to tune the band gap of the material and control the emission wavelength.

In some preferred embodiments substituents on $Ar^1$ may lead to a relatively large dihedral angle between $Ar^1$ and the chelating ring, e.g. 2-substituted pyridine, which may lead to a comparatively more isolated metal centre, which may alter the relative amounts of metal-to-ligand charge transfer (MLCT) and ligand-centred (LC) transitions of the metal-organic complexes formed containing the ligands of the invention, and thus the mixing of these states. This could manifest itself by changes in the optical properties of the metal-organic complex, such as (i) the pure radiative lifetime ($\tau_0$), (ii) the photoluminescence quantum yield (PLQY) and (iii) the emission wavelength ($\lambda_{emission}$). MLCT complexes arise from transfer of electrons from MO with metal-like character to those with ligand-like character. This is most commonly observed in complexes with ligands having low-lying $\pi^*$orbitals; especially aromatic ligands. The transition will occur at low energy if the metal ion has a low oxidation number, for its d orbitals will be relatively high in energy.

For example, in the structures shown below the complex with 1,4-phenylene units has a much smaller dihedral angle between the phenylene units and the pyridine ring than the m-xylene based structure has between the m-xylene rings and the pyridine ring. The dihedral angle between the m-xylene-based ring and pyridine-based ring increases due the steric clash between the methyl groups and the pyridine hydrogens. This twist caused by the m-xylene ring can reduce the conjugation and blue-shift the emission compared to a metal-organic complex containing just a 1,4-phenylene unit that does not exhibit any significant twist. For complexes with long arms and extensive conjugation, twists in the molecule may be desirable in order to restrict the red-shift of the emission.

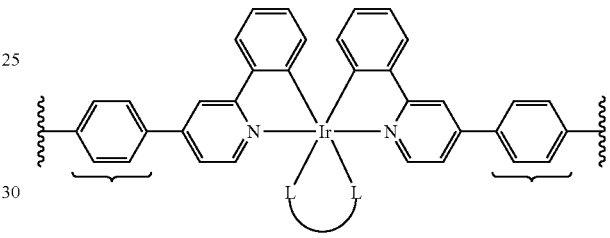

(with 1-4 phenylene units)

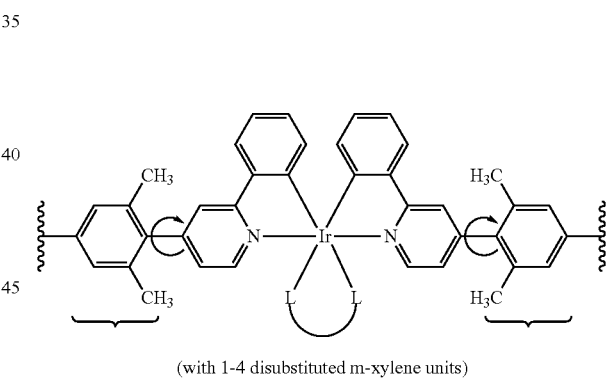

(with 1-4 disubstituted m-xylene units)

$Y^1$ and each $Y^2$ are independently an optionally substituted $C_2$ trans double-bond linking moiety. The optional substitution may include any electron-withdrawing or electron-donating group and can be used to tune the light emission of the molecule. For example, a preferred substitution group is a nitrile group.

$Y^1$ and $Y^2$ provide a method of linking aromatic or heteroaromatic ring systems and increasing the length of the chain of aromatic or heteroaromatic moieties without including more ring structures. Advantageously, the use of trans double bond linking moieties maintain the linear structure of the ligand and increases the aspect ratio of contiguous conjugated portion of the ligand. The aspect ratio of a molecule is the ratio of the ligand length to its width. Increasing the aspect ratio of the ligand may improve the performance of an emitter complex comprising the ligand.

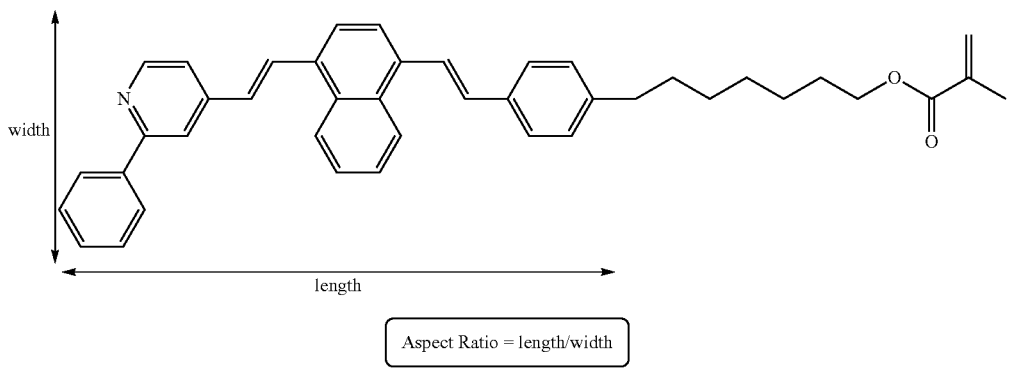 [SMILES: C=C(C)C(=O)OCCCCCCCc1ccc(/C=C/c2ccc(/C=C/c3ccnc(-c4ccccc4)c3)c3ccccc23)cc1]

Aspect Ratio = length/width

Additionally, the use of trans double bond linking moieties allows some further control of the emission wavelength. That is, compounds with phenyl-double bond-phenyl linkages are generally more red-shifted than compounds with phenyl-phenyl linkages. Phenylene vinylene and cyano-phenylene vinylene aromatic units may decrease the non-radiative decay constant ($K_{nr}$) and improve the PLQY of the metal-organic complexes.

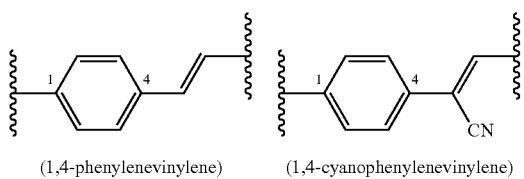

(1,4-phenylenevinylene)     (1,4-cyanophenylenevinylene)

These structures are particularly preferred combinations of an Ar group and a Y group. The substitution of the vinyl group with a nitrile group may effect the emissive behaviour due to its electron withdrawing nature.

"a" is 0, 1, 2 or 3. Preferably a is 0 or 1. The presence of the group $Ar^1$ group, especially when substituted, can improve the MLCT characteristics as discussed above.

"b" is 0, 1 or 2. Preferably b is 1 or 2 and most preferably 1. This requires that the group $Y^1$ is present in the ligand. The presence of the $Y^1$ group increases the aspect ratio and can be used to tune the emission.

Each "c" is independently 0, 1 or 2. Preferably c is 0 or 1. When it is 1 this requires that the group $Y^2$ is present in the ligand. The presence of the $Y^2$ group increases the aspect ratio and can be used to tune the emission. When d is 2, 3 or 4, preferably at least one c may be 0 to provide a chain of aryl groups.

"d" is 0, 1, 2, 3 or 4. Preferably d is 1 to 4, depending on the desired band gap. Larger values of d also help to achieve a larger aspect ratio.

S is a flexible spacer. In the present application a spacer group is a moiety connected at two distal ends to the adjacent moieties. Spacer groups are intended to introduce space and conformational flexibility, through rotatable bonds, between specific moieties in a molecular structure. This electrically isolates the emitter complex and allows the terminal cross linking groups B the requisite flexibility to efficiently cross-link with other cross-linkable groups in adjacent molecules.

Preferably S has the formula 2:

—K—$S^1$—K—    (2)

wherein $S^1$ is a straight chain or branched $C_4$-$C_{14}$ alkyl group, wherein from 1 to 10 $CH_2$ groups are optionally each replaced by an oxygen, provided that no acetal, ketal, peroxide or vinyl ether is present in the S group, and wherein each K is independently selected from a bond, or an ether, ester or carbonate linkage. Preferably S is achiral.

B represents a moiety having one or more cross-linkable functionalities. Preferably B is of the formula 3 or the formula 4:

—$B^1$    (3)

—Z(—S—$B^1$)$_2$    (4)

wherein $B^1$ is a cross-linkable functionality selected from the group consisting of ethylenic, diene, thiol and oxetane cross-linkable groups, wherein Z is a straight-chain $C_1$-$C_{12}$ alkyl, $C_1$-$C_{12}$ haloalkyl, $C_3$-$C_8$ cycloalkyl, $C_6$-$C_{16}$ aryl or $C_4$-$C_{15}$ heteroaryl group, and wherein S has the formula 2.

Preferably S or $S^1$ is a linear $C_7$ alkyl chain and/or wherein B is a vinyl ether or maleimide cross linking group.

Preferably the ring including the first ligand centre comprises a substantially linear substituent $T^2$ meta to the first ligand centre. $T^2$ also has the formula 1 above and may be the same or different from $T^1$. Moreover, $T^2$ is attached to the ring by $X^2$, wherein $X^2$ is a bond, a methylene group, a substituted methylene group, an oxygen atom or a sulphur atom, although it is preferred that $X^2$ is just a bond. $T^2$ is meta to the first ligand centre. That is, the two chains attached to the coordinating portion of the ligand are arranged to lie in a linear configuration relative to each other. In other words, where the ligand comprises $T^1$ and $T^2$ it is preferred that the two L groups are close to para to each other. That is, where the ligand comprises $T^1$ and $T^2$, preferred ligand positions are:

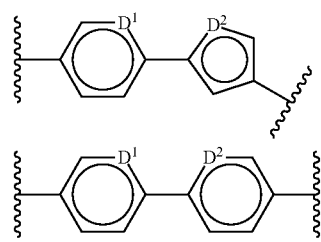

where $D^1$ and $D^2$ are the first and second ligand centres respectively

Where the ligand comprises only $T^1$ and the second ligand centre is in a 6-membered ring it is preferred that $T^1$ is para to the second ligand centre. That is, where the ligand comprises one $T^1$. The preferred ligand position is:

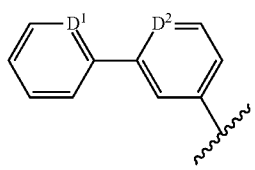

where $D^1$ and $D^2$ are the first and second ligand centres respectively

Where the ligand only comprises T1, a pair of such ligands may preferably be coordinated to the metal centre in order to provide a linear complex.

These ligand arrangements maintain a linear shape to the ligand and separate the cross-linking groups.

Organometallic compounds are compounds having at least one metal-to-carbon bond. Organometallic complexes are complexes containing a metal atom that is coordinated to at least one carbon ligand centre. In a further aspect the present invention provides a complex comprising one or more 1, 4 bidentate ligands described herein coordinated to iridium (III), platinum (II), osmium (II) or ruthenium (II). Preferred complexes comprise iridium (III) metal centres.

Preferred complexes have an octahedral bis-heteroleptic or tris-heteroleptic structure, or a square planar bis-homoleptic or bis-heteroleptic structure, for example an octahedral iridium complex or a square planar platinum complex. Heteroleptic, as used herein, refers to an organometallic compound having two or more types of ligand. Bis-heteroleptic complexes feature two different types of ligand and tris-heteroleptic complexes feature three different types of ligand.

Preferred complexes have two 1, 4 bidentate ligands each comprising the same $T^1$ and, where present, $T^2$ substituents. However, where two such ligands are present it is preferred that the ligands do not have $T^2$ substituents as this limits the linear form of the molecule.

In a further aspect the present invention provides a composition comprising the complex described herein and a nematic liquid crystalline material, wherein the nematic liquid crystalline material is preferably cross-linkable. Preferably the composition comprises from 1 to 50 wt % of the complex, more preferably from 5 to 30 wt %, with the remainder comprising the host nematic liquid crystalline material. Preferred examples of nematic liquid crystalline materials are those described in PCT/GB2015/051164 and GB1617087. Such structures are compatible with complexes of the present invention and have favourable material and electronic properties. Such materials are suitable as a host for the organometallic complexes of the present invention.

In a further aspect the present invention provides a network polymer formed by exposure of the ligand or the complex, or the composition described herein to radiation, optionally wherein said radiation in ultraviolet light.

In a further aspect the present invention provides a device comprising one or more charge transport layers and/or emissive layers comprising the network polymer according described above.

Preferably wherein the device is an OLED device, a photovoltaic device or a thin film transistor (TFT) device.

Preferably the network polymer is provided in a hole transporting layer or an electron transporting layer provided directly adjacent an electron transporting layer or a hole transporting layer respectively.

Preferably the device is an OLED device having a light emitting emissive layer and wherein the network polymer forms a uniformly aligned liquid crystalline structure within the emissive layer whereby the light emitting emissive layer emits linearly polarised light.

In a further aspect the present invention provides a method for forming a device as described above, the method comprising providing a layer comprising the ligand or the complex, or the composition described above, selectively irradiating the layer with radiation, preferably with UV radiation, to form a network polymer and washing away any non-irradiated and unpolymerised ligand or complex.

Preferably the above method further comprises providing a further layer comprising the ligand or the complex, or the composition described above, selectively irradiating the layer with radiation, preferably with UV radiation, to form a network polymer and washing away any non-irradiated and unpolymerised ligand or complex.

In a further aspect the present invention provides a device obtainable by the above method, the device comprising two or more network polymers each forming patterned structures, said structures being comprised of materials that are electroluminescent in nature, wherein the wavelength of electroluminescence emitted by one patterned structure is different to the wavelength of electroluminescence emitted by at least one other patterned structure.

The present invention provides a novel approach enabling the production of photo cross-linkable ligands for forming photo cross-linkable metal organic complexes.

The ligands of the present invention are suitable for forming metal organic complexes and include cross linking groups allowing the formation of polymers. The ligands include a chain of aromatic ring structures. Advantageously the chain has a large aspect ratio (length:width as shown above). The high aspect ratio may lead to alignment of the molecules and the molecules may exhibit a nematic liquid crystalline phase. The spacer groups provide the necessary flexibility between the conjugated portion of the molecules and the cross linking groups, allowing the conjugated portions to align even when the molecules are polymerised.

The liquid crystalline nature of network polymers comprising complexes of the present invention offer improved emission efficiency due to the alignment of the horizontal dipoles of the complexes. These structure yield greater emission efficiency out of the plane of the OLED material.

Advantageously, the complexes of the present invention exhibit lineal polarisation and may be used as backlight for liquid crystalline displays.

Various components of the present invention allow tuning of the emissive properties of the ligands/complexes. In particular, the following features may be altered to control the emissive properties and engineer the band gap:
  selection of the $Ar^1$ and $Ar^2$ groups;
  use of trans double bond linkers between aromatic ring structures;
  use of substituents on the aromatic and/or heteroaromatic groups in order to control the dihedral angle between aromatic and/or heteroaromatic groups;
  choice of the metal core; and
  use of electron donating and withdrawing substituents on the $Ar^1$, $Ar^2$, $Y^1$ and $Y^2$ groups.

According to a further aspect there is provided a 1, 4 bidentate ligand comprising first and second ligand centres, for synthesising the ligand described above and herein, wherein the first ligand centre is an sp²-hybridised carbon or a nitrogen atom;

wherein the second ligand centre is a nitrogen atom in a five- or six-membered aromatic or hetero-aromatic ring, said ring having a substantially linear substituent $T^1$ meta or para to the nitrogen atom;

wherein $T^1$ has the formula 1:

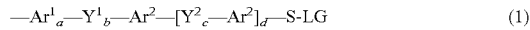 (1)

and wherein $T^1$ is attached to the ring by $X^1$, wherein $X^1$ is a bond, a methylene group, a substituted methylene group, an oxygen atom or a sulphur atom, wherein each $Ar^1$ and $Ar^2$ are independently selected from the group of $C_6$ to $C_{20}$ aromatic and $C_4$ to $C_{20}$ heteroaromatic groups, wherein $Y^1$ and each $Y^2$ is independently an optionally substituted $C_2$ or acetonitrile trans double-bond linking moiety, wherein a is 0, 1, 2 or 3,
wherein b is 0, 1 or 2,
wherein each c is independently 0, 1 or 2,
wherein d is 0, 1, 2, 3 or 4,
S is a flexible spacer, and
LG represents a leaving group.

LG is a leaving group, such as a hydroxy group (—OH), a halide (—Cl or —Br or —I), a sulfonate ester (such as a -mesylate or -tosylate), a carboxylate, phenoxide or any other conventional leaving group as would be known in the art.

This ligand can be used as it is in a liquid crystalline host, or as a synthetic intermediate to the production of the ligands and complexes discussed above.

According to a further aspect, there is provided a 1, 4 bidentate ligand comprising first and second ligand centres, wherein the first ligand centre is an sp²-hybridised carbon or a nitrogen atom; wherein the second ligand centre is a nitrogen atom in a five- or six-membered aromatic or hetero-aromatic ring, said ring having a substantially linear substituent $T^1$ meta or para to the nitrogen atom;

wherein $T^1$ has the formula 1:

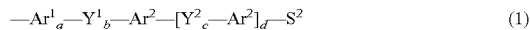 (1)

and wherein $T^1$ is attached to the ring by $X^1$, wherein $X^1$ is a bond, a methylene group, a substituted methylene group, an oxygen atom or a sulphur atom, wherein each $Ar^1$ and $Ar^2$ are independently selected from the group of $C_6$ to $C_{20}$ aromatic and $C_4$ to $C_{20}$ heteroaromatic groups, wherein $Y^1$ and each $Y^2$ is independently an optionally substituted $C_2$ or acetonitrile trans double-bond linking moiety, wherein a is 0, 1, 2 or 3,
wherein b is 0, 1 or 2,
wherein each c is independently 0, 1 or 2,
wherein d is 0, 1, 2, 3 or 4,
$S^2$ is a flexible spacer S terminated with H, or H.

This molecule can be made to align in a liquid crystalline host and produce anisotropic emission. These ligands can be used alone or in combination with those described herein.

PREFERRED EMBODIMENTS

Figure 1:
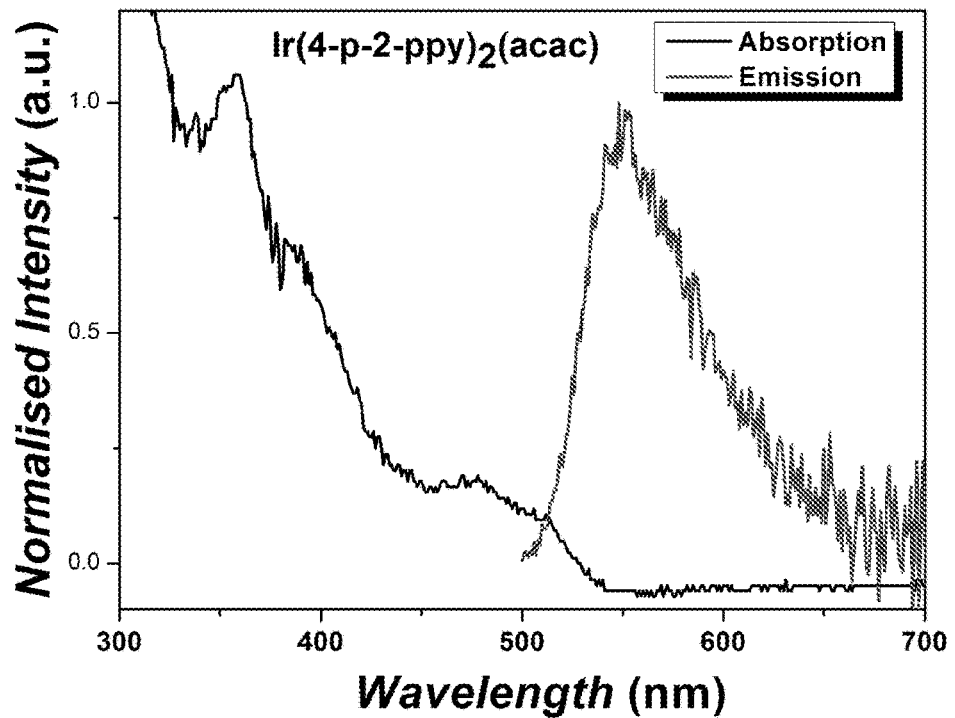
FIG. 1 is the normalised absorption and emission spectra of an iridium complex Ir(4-p-2-ppy)₂(acac) described herein in dilute toluene solution.
Figure 2:
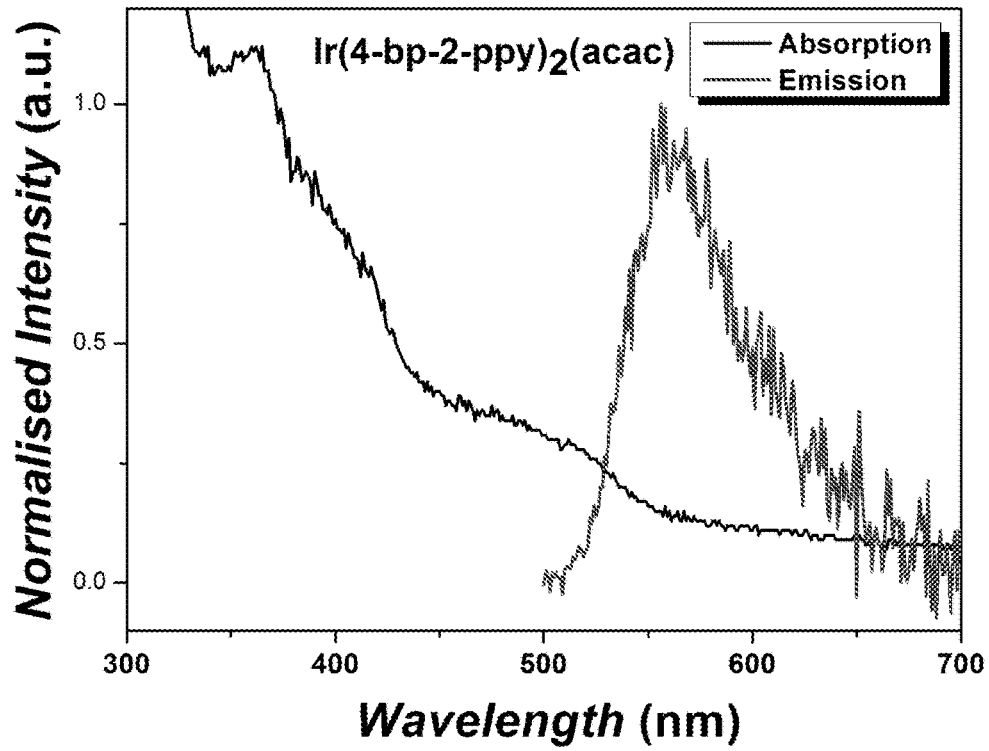
FIG. 2 is the normalised absorption and emission spectra of an iridium complex Ir(4-bp-2-ppy)₂(acac) described herein in dilute toluene solution.

In the following the structure of the 1,4-bidentate ligand described above will be referred to as L. The ligand L can form complexes with a transition metal M through the first and second ligand centres, which are referred to as P and Q respectively in the text which follows.

In the case of La, which is an embodiment of L, there is a linear arm of structure (I)

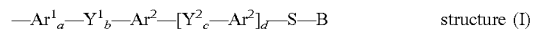 structure (I)

attached to the five membered ring ($Q^5$) or six membered ring ($Q^6$) containing the second ligand centre as appropriate via a bond, an optionally substituted bridging methylene group, an oxygen atom or a sulfur atom that is meta to the centre of $Q^5$ or para to the ligand centre of $Q^6$. a is 0, 1, 2 or 3. b is 0, 1 or 2. Each c is independently 0, 1 or 2. d is 0, 1, 2, 3 or 4. $Ar^1$ and $Ar^2$ are in each instance independently selected from the group of $C_6$ to $C_{20}$ aromatic and $C_4$ to $C_{20}$ heteroaromatic groups. S is a flexible spacer which in each occurrence is independently selected from the group of straight chain or branched achiral $C_4$-$C_{14}$ alkyl and ether groups linked to adjacent components of the arm through a bond or an ether, ester or carbonate linkage In the case of Lb, first and second linear arms of the structure (I) as defined above are attached meta to the ligand centres P and Q each of which form part of separate 6-membered aromatic rings, $P^6$ and $Q^6$.

In one embodiment there is provided a ligand Lc of the general structure L in which P is a sp² hybridised carbon and wherein Q and the components of the arm(s) of structure (I) are as defined above for La and Lb.

In one embodiment there is provided a ligand Ld of the general structure L in which P is a nitrogen atom and wherein Q and the components of the arm(s) of structure (I) are as defined above for La and Lb.

In one embodiment there is provided a ligand Le of the general structure L in which Q is a nitrogen and wherein P is a sp² hybridised carbon and forms part of a 6-membered aromatic ring and the components of the arm(s) of structure (I) are as defined above for La, Lb, Lc and Ld.

In one embodiment there is provided a ligand Lf of the general structure L in which Q is a nitrogen and forms part of a six membered aromatic ring and wherein P and the components of the arm(s) of structure (I) are as defined above for La, Lb, Lc and Ld.

In one embodiment there is provided a ligand Lg of the general structure La in which P is located within a five membered aromatic ring $P^5$ and wherein P and the components of the arm of structure (I) are as defined above for Lc, Ld, Le and Lf.

In one embodiment there is provided a ligand Lh of the general structure L in which P is located within a six membered aromatic ring $P^6$ and wherein P and the components of the arm(s) of structure (I) are as defined above for La, Lb, Lc, Ld, Le and Lf.

In one embodiment there is provided a ligand Lm of the general structure L in which $Ar^1$ and $Ar^2$ where present are in each instance independently selected from phenyl, naphthyl, fluorene, 9-9-dialkyl fluorene, 9-(1'-alkylidiene)fluorene, thiophene, furan and N-alkylcarbazole, oxadiazole, thiadiazole, pyridine, pyrimidine and tetrazine each of which are optionally substituted with one to four halogen and/or $C_1$-$C_6$-alkyl and/or $C_1$-$C_6$-alkoxy groups and wherein P, Q and the other components of the arm(s) of structure (I) are as defined above for La, Lb, Lc, Ld, Le, Lf, Lg, and Lh.

In one embodiment there is provided a ligand Ln of the general structure L in which Ar$^1$ and Ar$^2$ where present are phenyl groups optionally substituted with one to four halogen and/or C$_1$-C$_8$-alkyl and/or C$_1$-C$_6$-alkoxy groups and wherein P, Q and the other components of the arm(s) of structure (I) are as defined above for La, Lb, Lc, Ld, Le, Lf, Lg, and Lh.

In one embodiment there is provided a ligand Lo of the general structure L in which Ar$^1$ and Ar$^2$ where present are phenyl groups and wherein P, Q and the other components of the arm(s) of structure (I) are as defined above for La, Lb, Lc, Ld, Le, Lf, Lg, Lh, Lm and Ln.

In one embodiment there is provided a ligand Lp of the general structure L in which S is a flexible spacer which in each occurrence is independently selected from the group of straight chain or branched achiral C$_5$-C$_{14}$ alkyl groups and wherein P, Q and the other components of the arm(s) of structure (I) are as defined above for La, Lb, Lc, Ld, Le, Lf, Lg, Lh, Lm, Ln and Lo.

In one embodiment there is provided a ligand Lq of the general structure L in which S is a flexible spacer which in each occurrence is independently selected from the group of straight chain C$_5$-C$_{12}$ alkyl groups and wherein P, Q and the other components of the arm(s) of structure (I) are as defined above for La, Lb, Lc, Ld, Le, Lf, Lg, Lh, Lm, Ln and Lo.

In one embodiment there is provided a ligand Lr of the general structure L in which each B is independently selected from the group of alkene, diene, thiol and oxetane cross-linkable groups wherein P, Q and the other components of the arm(s) of structure (I) are as defined above for La, Lb, Lc, Ld, Le, Lf, Lg, Lh, Lm, Ln, Lo, Lp and Lq.

In one embodiment there is provided a ligand Ls of the general structure L in which each B is independently selected from the group of alkene cross-linkable groups wherein P, Q and the other components of the arm(s) of structure (I) are as defined above for La, Lb, Lc, Ld, Le, Lf, Lg, Lh, Lm, Ln, Lo, Lp and Lq.

In one embodiment there is provided a ligand Lt of the general structure L in which each B is independently selected from the group of cross-linkable groups that undergo cross-link on exposure to radiation, for example UV light wherein P, Q and the other components of the arm(s) of structure (I) are as defined above for La, Lb, Lc, Ld, Le, Lf, Lg, Lh, Lm, Ln, Lo, Lp and Lq.

In one embodiment there is provided a ligand Lu of the general structure L in which each B is independently selected from straight chain and cyclic ☐☐☐-unsaturated esters, ☐☐☐-unsaturated amides, vinyl ethers and non-conjugated diene cross-link groups wherein P, Q and the other components of the arm(s) of structure (I) are as defined above for La, Lb, Lc, Ld, Le, Lf, Lg, Lh, Lm, Ln, Lo, Lp and Lq.

In one embodiment there is provided a ligand Lv of the general structure L in which each B is independently selected from methacrylate, ethacrylate, ethylmaleato, ethylfumarato, N-maleimido, vinyloxy, alkylvinyloxy, vinylmaleato, vinylfumarato, N-(2-vinyloxymaleimido), 1,4-pentadien-3-yl and 1,4-cyclohexadienyl and wherein P, Q and the other components of the arm(s) of structure (I) are as defined above for La, Lb, Lc, Ld, Le, Lf, Lg, Lh, Lm, Ln, Lo, Lp and Lq.

In one embodiment there is provided a ligand Lw of the general structure L in which each B is independently selected from electron-rich alkene cross-linkable groups, for example an ethylene group substituted with one or more electron donating groups selected from O, N or S and wherein P, Q and the other components of the arm(s) of structure (I) are as defined above for La, Lb, Lc, Ld, Le, Lf, Lg, Lh, Lm, Ln, Lo, Lp and Lq.

In one embodiment there is provided a ligand Lx of the general structure L in which each B is independently selected from electron-rich alkene cross-linkable groups, for example a cyclic or acyclic vinyl ether group and wherein P, Q and the other components of the arm(s) of structure (I) are as defined above for La, Lb, Lc, Ld, Le, Lf, Lg, Lh, Lm, Ln, Lo, Lp and Lq.

In a further aspect the invention provides a complex C comprising a ligand of structure L (e.g. La, Lb, Lc, Ld, Le, Lf, Lg, Lh, Lm, Ln, Lo, Lp, Lq, Lr, Ls, Lt, Lu, Lv, Lw and Lx) as described above coordinated to iridium (III), osmium (II), ruthenium (II) and platinum (II).

In one embodiment there is provided an octahedral bis-heteroleptic or tris-heteroleptic complex Ca comprising one or two ligands of structure La (e.g. Lc, Ld, Le, Lf, Lg, Lh, Lm, Ln, Lo, Lp, Lq, Lr, Ls, Lt, Lu, Lv, Lw and Lx) as described above coordinated to iridium (III), osmium (II) or ruthenium (II).

In one embodiment there is provided a octahedral bis-heteroleptic or tris-heteroleptic organometallic complex Cb comprising one or two ligands of structure La (e.g. Lc, Ld, Le, Lf, Lg, Lh, Lm, Ln, Lo, Lp, Lq, Lr, Ls, Lt, Lu, Lv, Lw and Lx) as described above coordinated to iridium (III).

In one embodiment there is provided a octahedral bis-heteroleptic or tris-heteroleptic complex Cc of structure (Ia)

$$L^1L^2MA \qquad (Ia)$$

wherein L$^1$ and L$^2$ are 1,4-bidentate ligands that each coordinate to M through a) a first ligand centre that is an sp$^2$-hybridised carbon or nitrogen and b) a second ligand centre that is a nitrogen atom or an sp$^2$-hybridised carbon that is part of a 5- or 6-membered aromatic ring. The second ligand centres of L$^1$ and L$^2$ in the complex are trans to each other and at least one of L$^1$ and L$^2$ is of structure La (e.g. Lc, Ld, Le, Lf, Lg, Lh, Lm, Ln, Lo, Lp, Lq, Lr, Ls, Lt, Lu, Lv, Lw and Lx) as described above. M is selected from iridium (III), platinum (II), ruthenium (II) or osmium (II). A is a bidentate ancillary ligand or a pair of independently selected monodentate ancillary ligands. Preferably the monodentate ligands are identical.

In one embodiment Cd the metal in Cc is iridium (III).

In one embodiment Ce the ancillary ligands A in complex Cc or Cd are monodentate and are selected from friaryl phosphines (Ar$_3$P), trialkyl phosphines (R$_3$P), cyanide ions (CN$^-$), halides (F$^-$, Cl$^-$, Br$^-$), isocyanides (RNC) and carbonyls (CO).

In one embodiment Cf the ancillary ligand A in complex Cc or Cd is bidentate and is selected from acetylacetonate (acac), R$^1$COCHCOR$^2$ where R$^1$ and R$^2$ are optionally substituted C$_2$-C$_8$ alkyl or C$_6$-C$_{10}$ aryl groups, diphosphines containing two diphenyl phosphines linked by a C$_2$-C$_6$ bridging alkyl group and picolinate.

In one embodiment Cg the complex Cc, Cd, Ce or Cf is bis-heteroleptic, i.e. L$^1$ and L$^2$ are identical.

In one embodiment Ch the complex Cc, Cd, Ce or Cf is tris-heteroleptic and L$^2$ is a bidentate ligand selected from 2-phenylpyridine, 2-napthylpyridine, 2-(2,4-difluorophenyl) pyridine, 2,2'-bipyridine, 1,10-phenanthroline, benzo[h]quinoline, 2-(2-thienyl)pyridine, pyridine-1,2,4-triazole, 2-phenylbenzo[d]oxazole, alkenylpyridine, phenylpyrazole, phenylimidazole, phenyltetrazoles and phenylquinoxalines.

In one embodiment Ci the complex Cc, Cd, Ce or Cf is tris-heteroleptic and L$^2$ is a bidentate ligand selected from 2-phenylpyridine, 2-napthylpyridine, 2-(2,4-difluorophenyl) pyridine, 2,2'-bipyridine, 2-(2-thienyl)pyridine, pyridine-1, 2,4-triazole, 2-phenylbenzo[d]oxazole, alkenylpyridine, phenylpyrazole, phenylimidazole and phenyltetrazoles.

In one embodiment there is provided a square planar complex Cj comprising a ligand of structure Lb (e.g. Lc, Ld, Le, Lf, Lg, Lh, Lm, Ln, Lo, Lp, Lq, Lr, Ls, Lt, Lu, Lv, Lw and Lx) as described above coordinated to platinum (II).

In one embodiment Ck there is provided a complex Cj with one ligand of structure Lb (e.g. Lc, Ld, Le, Lf, Lg, Lh, Lm, Ln, Lo, Lp, Lq, Lr, Ls, Lt, Lu, Lv, Lw and Lx) and an ancillary ligand A that is a bidentate ancillary ligand or a pair of monodentate ancillary ligands.

In one embodiment Cl the ancillary ligand in Ck is a bidentate ancillary ligand selected from acetylacetonate (acac), $R^1COCHCOR^2$ where $R^1$ and $R^2$ are $C_2$-$C_8$ alkyl or $C_6$-$C_{10}$ aryl groups, diphosphines containing two diphenyl phosphines linked by a $C_2$-$C_6$ bridging alkyl group and picolinate.

In a further aspect there is provided use of a ligand of structure L, for example La, Lb, Lc, Ld, Le, Lf, Lg, Lh, Lm, Ln, Lo, Lp, Lq, Lr, Ls, Lt, Lu, Lv, Lw and Lx, in the emissive layer of an OLED device.

In one embodiment there is provided use of a complex of structure C, for example Ca, Cb, Cc, Cd, Ce, Cf, Cg, Ch, Ci, Cj, Ck, or Cl, as a phosphor in the emissive layer of an OLED device.

In one aspect there is provided a method for making an OLED device comprising the step of depositing a complex of structure C for example Ca, Cb, Cc, Cd, Ce, Cf, Cg, Ch. Ci, Cj, Ck, or Cl, onto a substrate, optionally a liquid crystalline substrate, and then exposing to radiation, optionally UV light.

In one aspect there is provided an OLED device comprising a complex of structure C, for example Ca, Cb, Cc, Cd, Ce, Cf, Cg, Ch. Ci, Cj, Ck, or Cl, in its emissive layer.

In one embodiment there is provided an OLED device comprising a complex of structure C, for example Ca, Cb, Cc, Cd, Ce, Cf, Cg, Ch. Ci, Cj, Ck, or Cl, aligned on a liquid crystalline material in its emissive layer.

DETAILED DESCRIPTION

Chemical terminology used herein has the normal meaning as defined in the IUPAC Gold Book (http://goldbook.iupac.org/). For ease of reference, simple definitions for some of the terminology used herein is provided below.

In general, the term "Alkyl" is used herein refers to straight chain or branched chain alkyl, such as, without limitation, methyl, ethyl, n-propyl, iso-propyl, butyl, n-butyl and tert-butyl. Straight chain alkyl is generally preferred unless otherwise indicated. In some cases a methylene ($CH_2$) group in the alkyl chain can be replaced with an heteroatom such as oxygen, sulphur or nitrogen. In the case where a methylene group is replaced by a nitrogen it is preferred that the nitrogen is additionally substituted with a $C_1$-$C_6$ alkyl group.

In general, the term "Aryl" as used herein refers to aromatic ring structures. Preferred aromatic ring structures are $C_6$ to $C_{18}$ aromatic groups including phenyl, naphthyl, fluorenyl, anthracenyl, pyrenyl and $C_4$ to $C_{12}$ heteroaromatic groups including imidazole, triazole, tetrazole, pyrazole, pyridine, pyridazine, pyrrole, thiophene, furan, oxazole, isoxazole, benzisoxazole and N-alkylcarbazole. For further examples see the description of $Ar^1$ and $Ar^2$ below.

Alkoxy as used herein refers to straight or branched chain alkoxy, for example methoxy, ethoxy, propoxy, butoxy. Alkoxy as employed herein also extends to embodiments in which the or an oxygen atom (e.g. a single oxygen atom) is located within the alkyl chain, for example —$C_{1-3}$ alkyl$OC_{1-3}$ alkyl, such as —$CH_2CH_2OCH_3$ or —$CH_2OCH_3$.

Halo or halogen includes fluoro, chloro, bromo or iodo, in particular fluoro, chloro or bromo, especially fluoro or chloro.

Heteroleptic, as used herein, refers to an organometallic compound having two or more types of ligand. Bis-heteroleptic complexes feature two different types of ligand and tris-heteroleptic complexes feature three different types of ligand.

Organometallic compounds are compounds having at least one metal-to-carbon bond. Organometallic complexes are complexes containing a metal atom that is coordinated to at least one carbon ligand centre. A ligand centre is the atom of a ligand that chemically binds to a metal atom in a complex. An $sp^2$-hybridised carbon ligand centre is a carbon atom that is covalently double bonded to an adjacent atom in the ligand and that forms a chemical bond to a metal atom in the overall organometallic complex. Preferred ligands of the inventions form complexes with useful light emitting properties. Preferred materials of the invention are complexes of iridium (III), platinum (II), osmium (II) and ruthenium (II).

In most preferred examples the metal complex is an iridium (III). Iridium (III) and platinum (II) possess the most attractive properties for OLED applications due to their higher triplet quantum yield ($\Phi_P$), relatively short triplet state lifetime ($\tau_P$), and tunable emission colour.

Monodentate ligands are ligands that can form a chemical bond to a metal atom through a single ligand centre. Examples of monodentate ligands described herein that are useful as ancillary ligands include but are not limited to triaryl phosphines ($Ar_3P$), trialkyl phosphines ($R_3P$), cyanide ions ($CN^-$), halides ($F^-$, $Cl^-$, $Br^-$), isocyanides (RNC) and carbonyls (CO).

Bidentate ligands are ligands that, when part of a ligand-metal complex, have two ligand centres that can form chemical bonds to a metal atom. 1,4-Bidentate ligands are bidentate ligands with two ligand centres separated by three chemical bonds. An example of a 1,4-bidentate ligand is given below with the ligand centres indicated by an asterisk.

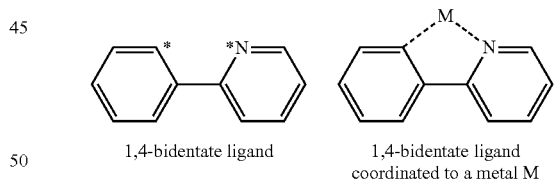

1,4-bidentate ligand        1,4-bidentate ligand
                            coordinated to a metal M The 5- or 6-membered aromatic ring structures of the bidentate ligands referred to herein are 6☐-electron conjugated nitrogen heterocycles that optionally contain one or more further heteroatoms. Examples of 5-membered nitrogen heterocycles described herein include pyrrole, imidazole, pyrazole, triazole, tetrazole, oxazole, isoxazole, isothiazole, oxadiazole and thiadiazole and all of the isomeric forms of these structures. Examples of 6-membered nitrogen heterocycles described herein include pyridine, pyridazine, pyrimidine, pyrazine, triazine and tetrazine and all of the isomeric forms of these structures. Benzo derivatives of these 5- and 6 membered are also encompassed in the description, such benzo-derivatives feature a 6-membered aromatic ring fused to the 5- or 6-membered nitrogen heterocycles described above and include, by way of example, quinoline, isoquinoline, quinazoline, quinoxaline, phthalazine, indole, benzimidazole and benzisoxazole. 2-Phenyl pyridine systems and analogues are most preferred.

The term ancillary ligand refers to a ligand or ligands that fulfil the valency and electronic requirements required to stabilise the organometallic complex but have no considerable influence on the chemistry of the complex. Examples of bidentate ancillary ligands include acetylacetonate (acac) and related ligands described by the general structure $R^1COCHCOR^2$ where $R^1$ and $R^2$ are alkyl or aryl groups, diphosphines containing two diphenyl phosphines linked by a bridging $C_2$-$C_6$ alkyl group such as dppe, dppp and dppb (with ethyl, propyl and butyl bridging groups respectively), quinolinate and picolinate.

Exemplary ancillary ligands are:

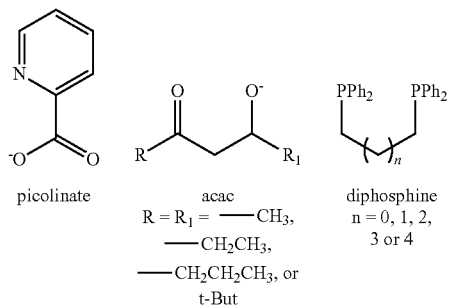

picolinate acac
R = R₁ = ——CH₃,
——CH₂CH₃,
——CH₂CH₂CH₃, or
t-But diphosphine
n = 0, 1, 2,
3 or 4

The term "arm" is used to refer to a linear structure of formula 1:

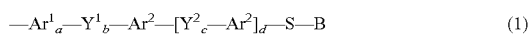 (1)

attached to $Q^5$ or $Q^6$ (i.e. the ring containing the second ligand centre having 5 or six constituent atoms) as appropriate, wherein (1) is attached to the ring by X, wherein X is a bond, a methylene group, a substituted methylene group, an oxygen atom or a sulphur atom.

Each $Ar^1$ and $Ar^2$ are independently selected from the group of $C_6$ to $C_{20}$ aromatic and $C_4$ to $C_{20}$ heteroaromatic groups. $Y^1$ and each $Y^2$ is independently an optionally substituted $C_2$ or acetonitrile trans double-bond linking moiety. a is 0, 1, 2 or 3. b is 0, 1 or 2. Each c is independently 0, 1 or 2. d is 0, 1, 2, 3 or 4. S is a flexible spacer, and B represents a moiety having one or more cross-linkable functionalities The $Ar^1$ and $Ar^2$ groups are connected to adjacent members of the arm to maintain the linear character of the arms. As well as providing alignment properties with e.g. liquid crystalline host materials or liquid crystalline aligned substrate layers derived from e.g. π-π interactions, these groups can be used to tailor the electron and hole transport characteristics of the material. Thus $Ar^1$ and $Ar^2$ can be used to optimise the efficiency of the light emission of complexes of the invention in e.g. an OLED device. In addition, the electronic properties of the $Ar^1$ group, and to a lesser extent the $Ar^2$ group can alter the wavelength of light emitted by the complexes of the invention as they influence the energy levels of the molecular orbitals of the overall complex and the energy gap between the metal-ligand orbitals through which excited complexes degrade and release light.

In cases where $Ar^1$ or $Ar^2$ are 5-membered rings they are substituted by adjacent components of the arm at the 1,3- or 1,4-positions (e.g. when the heteroatom is N) or at 2,4- or 2,5-positions (e.g. where the heteroatom is S, N or O).

Where the $Ar^1$ or $Ar^2$ groups are 6-membered rings such as phenyl they are substituted by adjacent components of the arm at the 1- and 4-positions. In the case where the $Ar^1$ and $Ar^2$ groups are 10-membered bicycles such as naphthyl they are substituted by adjacent components of the arm at the 1,4-, 1,5- or 2,6-positions. In the case where the $Ar^1$ and $Ar^2$ groups are linear 14-membered tricycles such as anthracenyl they are substituted by adjacent components of the arm at the 2,6-positions. In the case where the $Ar^1$ and $Ar^2$ group are linear 14-membered tricycles such as phenanthracenyl they are substituted by adjacent components of the arm at the 1,4- and 1,7-positions. In the case where the $Ar^1$ and $Ar^2$ group are 16-membered tetracycles such as pyrenyl they are substituted by adjacent components of the arm at the 1,4- and 1,7-positions. As will be appreciated, the presence of heteroatoms would change the official numbering of the locations in the molecule—for consistency, the numbering should be approached as if the molecules are entirely carbon atom structures.

Each $Ar^1$ and $Ar^2$ are independently selected from the group of optionally substituted $C_6$ to $C_{20}$ aromatic and $C_4$ to $C_{20}$ heteroaromatic groups. Preferably each $Ar^1$ and $Ar^2$ are optionally substituted aromatic diradicals independently selected from the group consisting of 1,4-phenylene, naphthalene-1,4-diyl, naphthalene-2,6-diyl, perylene-3,10-diyl, pyrene-2,7-diyl, fluorene-2,7-diyl, fluorene-3,6-diyl, 9,9-dialkylfluorene-2,7-diyl, 9,9-dialkylfluorene-3,6-diyl, 9-(1'-alkylidiene)fluorene-2,7-diyl, 2,5-dialkoxybenzene-1,4-diyl, m-xylene, p-xylene, durene and/or optionally substituted heteroaromatic diradicals independently selected from the group consisting of benzo[1,2-b:4,5-b']bis[1]benzothiophene-3,9-diyl, dibenzothiophene-3,7-diyl, [1]benzothieno[3,2-b][1]benzothiophene-2,7-diyl, 1,3,4-oxadiazole-2,5-diyl, 1,3,4-thiadiazole-2,5-diyl, 2,1,3-benzothiadiazole-4,7-diyl, 2,2'-dithiophene-5,5'-diyl, 4,7-dithien-2-yl-2,1,3-benzothiazole-5',5"-diyl, 4-alkyl-1,2,4-triazole-3,5-diyl, 4-thien-2-yl-2,1,3-benzothiazole-7,5'-diyl, 5,5-dioxodibenzothiophene-3,7-diyl, 5,11-dialkylindolo[3,2-b]carbazole-3,9-diyl, 5,11-dihydroindolo[3,2-b]carbazole-2,8-diyl, 9-alkylcarbazole-2,7-diyl, 9-alkylcarbazole-3,6-diyl, benzo[1,2-b:4,5-b']dithiophene-2,6-diyl, benzo[1,2-b:5,4b']dithiophene-2,6-diyl, benzo[1,2-d:4,5-d]bisoxazole-2,6-diyl, benzo[1,2-d:5,4-d]bisoxazole-2,6-diyl, dithieno[3,2-b:2',3'-d]thiophene-2,6-diyl, imidazo[4,5-d]imidazole-2,5-diyl, oxazole-2,5-diyl, oxazolo[4,5-d]oxazole-2,5-diyl, oxazolo[5,4-d]oxazole-2,5-diyl, pyridine-2,5-diyl, pyrimidine-2,5-diyl, 5,5-dialkyl-5H-dibenzo[b,d]silole, pyridine-2,5-diyl, pyrimidine-2,5-diyl, thiazolo[4,5-d]oxazole-2,5-diyl, thiazolo[4,5-d]thiazole-2,5-diyl, thiazolo[5,4-d]oxazole-2,5-diyl, thiazolo[5,4-d]thiazole-2,5-diyl, thieno[3,2-b]thiophene-2,5-diyl, thiophene-2,5-diyl, furan-2,5-diyl and 1,2,4,5-tetrazine-3,6-diyl.

If hole transporting properties are desired then indole and thiophene containing moieties such as those presented below may be preferred, * denotes the typical site of attachment.

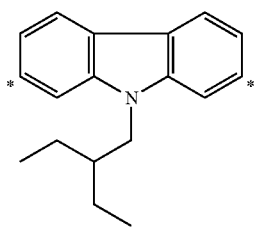

-continued

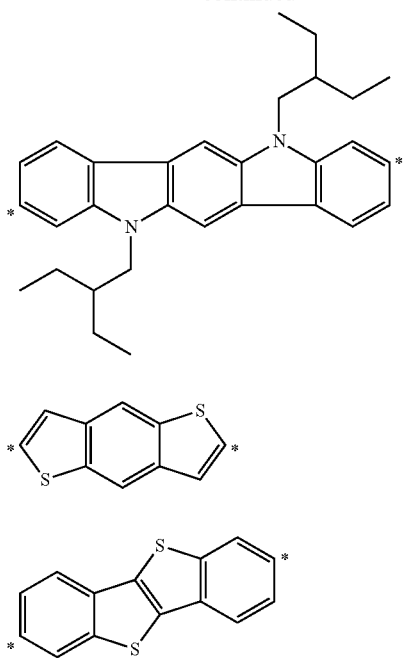

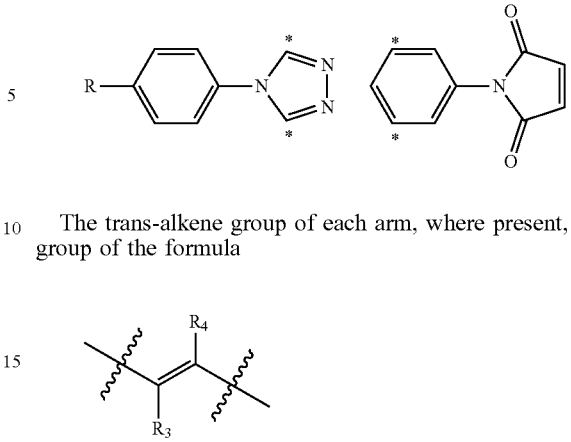

The trans-alkene group of each arm, where present, is a group of the formula

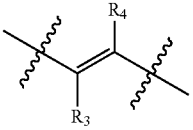

wherein $R^3$ and $R^4$ are trans to each other and are each either H, $C_{1-4}$ alkyl or CN groups. Where $R^3$ or $R^4$ are alkyl, methyl and ethyl groups are preferred.

The composition of the arm is such that overall the arm is a linear conjugated system terminating in an insulating spacer group S, optionally with a site of branching Z, and a cross-linkable group B (or in the case where Z is present in two cross-linkable groups B and $B^1$. The linear character and the presence of a number of aromatic and/or heteroaromatic rings in the arm confers the ability to of the ligand, and by extension the complexes it forms to align with liquid crystalline materials that surround them in the device thus providing the opportunity to obtain OLED device structures wherein the emitter cores are substantially all aligned in the same direction, for example by aligning with a liquid crystalline host material. This advantageously allows the possibility to deliver emitter layers with anisotropic emission characteristics and improved light output due to a reduction in the light absorbed by the device.

If electron transporting properties are desired then oxazole containing moieties such as those presented below may be preferred, * denotes the typical site of attachment.

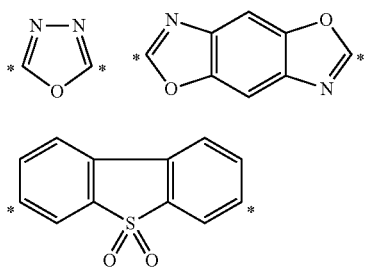

The $Ar^1$ and $Ar^2$ groups of each arm may be optionally substituted with one to four halogens or alkyl groups. Preferred substituents are F, Cl, $CF_3$ and $C_{1-5}$ alkyl groups. It is preferred that the $Ar^1$ and $Ar^2$ groups of each arm are selected independently from the group of $C_6$ to $C_{18}$ aromatic groups with no intrinsic fluorescence properties of their own—for this reason aromatic groups such as anthracene and phenanthracene are generally not preferred. Examples of preferred $Ar^1$ and $Ar^2$ groups are phenyl, biphenyl, naphthyl, terphenyl, 9,9-dialkylfluorene, thiophene and N-alkyl carbazole. In some cases it is preferred that $Ar^1$ and $Ar^2$ are optionally substituted phenyl or naphthyl. In preferred cases $Ar^1$ and $Ar^2$ are optionally substituted phenyl. In most preferred cases $Ar^1$ and $Ar^2$ are phenyl.

Such moieties provided as substituents which do not extend the arm length are not counted in the formula of the arm (1). That is, moieties in the arm may be substituted with other aromatic or heteroaromatic rings. For example, due to the position of the attachment, each of the following structures would constitute a single moiety in the arm.

In some preferred embodiments the integer a is 0, b is 1, each c is 1, d is from 1 to 5, and X is a bond. An example of an arm unit with this structure is

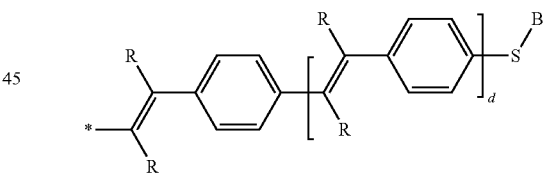

wherein the asterisk indicates the site of attachment to the rest of the ligand and benzene is used to represent each Ar group.

In some preferred embodiments the integer d is from 2 to 5. In some preferred embodiments the integer d is from 3 to 5. In some preferred embodiments d is either 2 or 3.

In some preferred embodiments the integer a is 1, b is 1, each c is 0, d is from 1 to 5 and X is a methylene. An example of an arm unit with this structure is

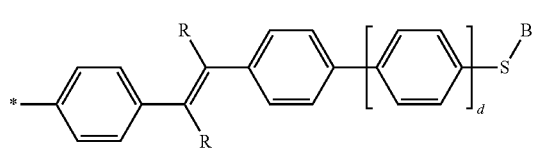

wherein the asterisk indicates the site of attachment to the rest of the ligand and benzene is used to represent each Ar group.

S is a flexible spacer connected at two distal ends to the adjacent moieties which in each occurrence is independently selected from the group of straight chain or branched achiral $C_4$-$C_{14}$ alkyl and ether groups linked to adjacent components of the arm through a bond or an ether, ester or carbonate linkage. The spacer group serves, to a degree, to electrically isolate the emitter complex and also allows the cross-linkable groups B the requisite flexibility to efficiently cross-link with other cross-linkable groups in adjacent molecules. The compounds of the present invention are chemically stable enough to be used in OLED devices, spacer structures featuring relatively unstable groups such as acetals, ketals and peroxide groups do not form part of the present invention.

In some preferred embodiments the flexible spacer group S is a straight chain $C_{5-12}$ alkyl group. In some preferred embodiments the flexible spacer group S is a straight chain $C_{4-11}$ alkoxyalkyl group. In some preferred embodiments the flexible spacer group S is a straight chain $C_{3-10}$ polyether group.

Preferably S has the formula 2:

$$-K-S^1-K- \quad (2)$$

wherein $S^1$ is a straight chain or branched $C_4$-$C_{14}$ alkyl group, wherein from 1 to 10 $CH_2$ groups are optionally each replaced by an oxygen, provided that no acetal, ketal, peroxide or vinyl ether is present in the S group, and wherein each K is independently selected from a bond, or an ether, ester or carbonate linkage. Preferably S is achiral.

Preferably B is of the formula 3 or the formula 4:

$$-B^1 \quad (3)$$

$$-Z(-S-B^1)_2 \quad (4)$$

wherein $B^1$ is a cross-linkable functionality selected from the group consisting of ethylenic, diene, thiol and oxetane cross-linkable groups, wherein Z is a straight-chain $C_1$-$C_{12}$ alkyl, $C_1$-$C_{12}$ haloalkyl, $C_3$-$C_8$ cycloalkyl, $C_6$-$C_{16}$ aryl or $C_4$-$C_{15}$ heteroaryl group, and wherein S has the formula 2.

Branching, as in structure (4) can be advantageous when the metal complex contains a single ligand of structure L as a higher degree of cross-link can be obtained.

Preferably S or $S^1$ is a linear C7 alkyl chain and/or wherein B is methacrylate.

Exemplary —S—B groups are presented below by way of illustration wherein the asterisk indicates the site of attachment to the rest of the ligand.

Exemplary —B groups of the formula 4 are presented below by way of illustration wherein the asterisk indicates the site of attachment to the rest of the ligand through the flexible spacer S. The integers m, n and p are selected are chosen to match the preferred S structures described herein.

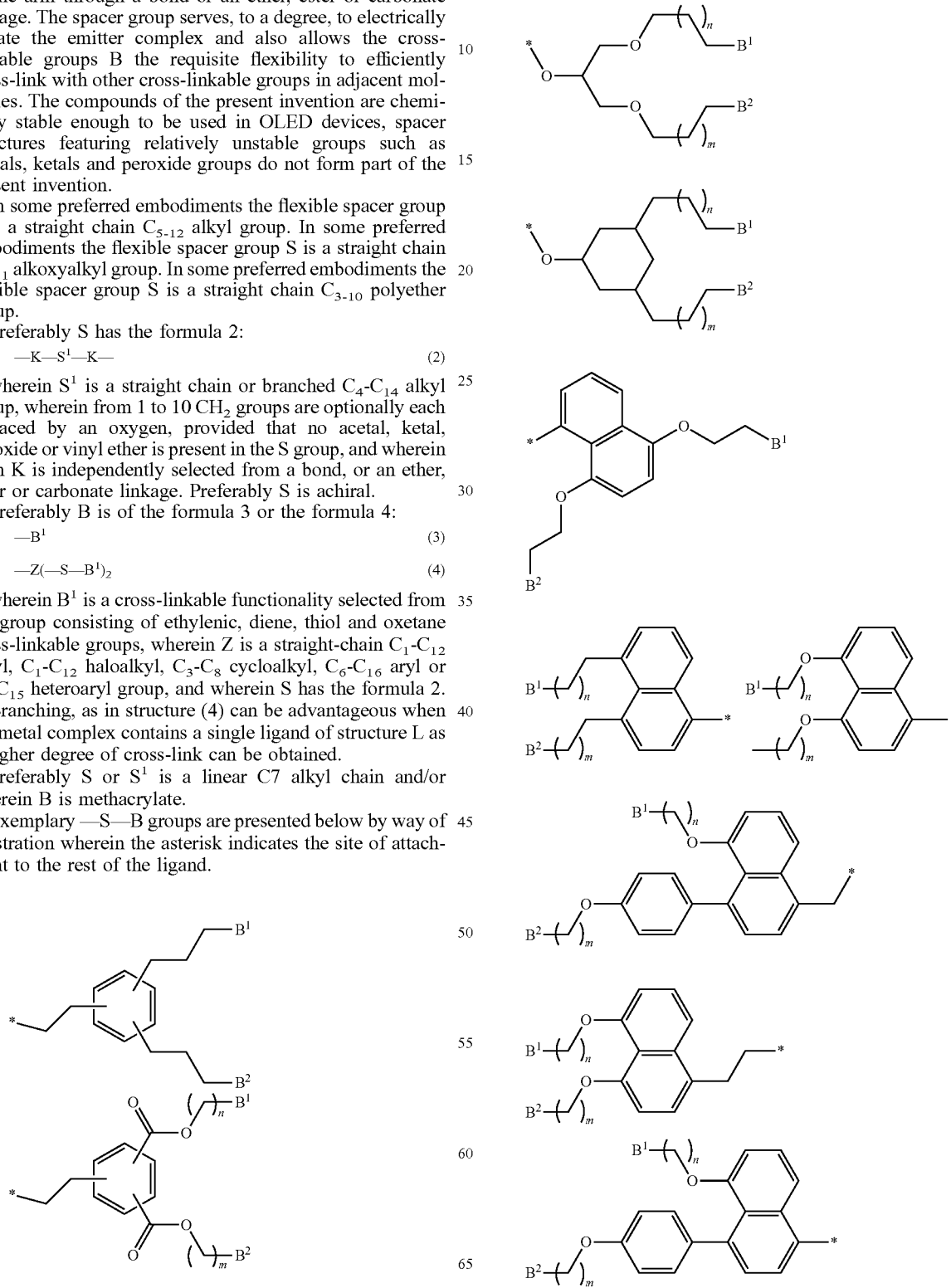

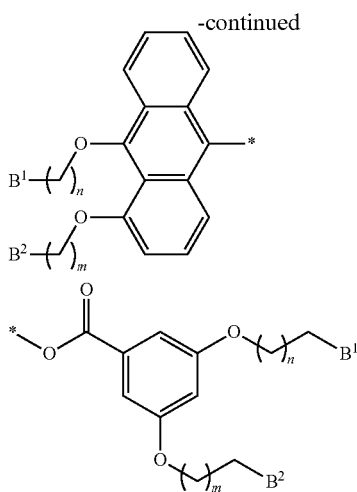

Preferred cross-link groups B (also referred to as cross-linkable groups herein) are selected from the group of alkene, diene, thiol and oxetane cross-linkable groups. Alkene or "ethylenic" cross-linkable groups are cross-linkable groups containing a carbon-carbon double bond. In a preferred aspect, all of the cross-link groups independently represent an alkene cross-link group. Favoured alkene cross-link groups include electron rich and electron poor ethylenic cross-link groups.

The compounds of the invention therefore comprise a first cross-link group B, and optionally a second cross-link group B, and form, when cross-linked, network polymers. This is because preferred cross-link groups react with two other cross-link groups to yield a chain reaction and a polymer matrix.

If the compounds of the present invention only have a single cross-linking group, then they will be unable to form a network polymer, except when provided in combination with a secondary monomer (or polymer) having two or more cross-linking grounds.

In a preferred aspect, polymerisable cross-linking groups are selected from the group of ethylenic, diene, thiol and oxetane polymerisable cross-linking groups. Ethylenic cross-linking groups are cross-linkable groups containing a carbon-carbon double bond. In a preferred aspect, all of the cross-link groups independently represent an ethylenic cross-link group. Favoured ethylenic cross-link groups include electron rich and electron poor ethylenic cross-link groups.

In a preferred aspect the cross-linkable groups undergo cross-link reactions on exposure to radiation. In a preferred aspect the cross-linkable groups are photo cross-linkable groups, i.e. those groups that undergo cross-link reactions on exposure to ultra-violet (UV) light.

Examples of preferred cross-linking groups are straight chain and cyclic ☐☐☐-unsaturated esters and ☐☐☐-unsaturated amides, straight chain terminal alkenes, bridged cyclic alkenes, thiols, vinyl ethers, cyclic ethers and non-conjugated dienes. Favoured cross-linking groups therefore include acrylate, methacrylate, monomethylmaleate, monoethylmaleate, monomethylfumarate, monoethylfumarate, 4,4,4-trifluorocrotonate, N-maleimide, ethenyl, N-vinylpyrrolidone, N-substituted-N-vinylformamide, N-substituted-N-vinylalkylamide, norbornene, sulfhydryl, vinyloxy, methylvinyloxy, 1,3-propylene oxide (oxetane), 1,4-pentadiene, 1,6-heptadiene and diallylamine as these groups are particularly suitable for photo cross-linking, especially with UV-light.

In a preferred aspect the cross-linking groups are electron-rich ethylenic cross-linkable groups. Electron rich ethylenic cross-linkable groups contain an ethylene group substituted with one or more electron donating groups. The electron donating group can comprise a heteroatom such as O, N or S. In a preferred aspect the electron rich cross-linkable group is a vinyloxy group. Other electron donating group substituted crosslinking groups are 1-alkenyl ethers such as propen-1-yloxy groups and buten-1-yloxy groups; cyclic vinyl ethers such as cyclohexen-1-yloxy and cyclopenten-1-yloxy; bicyclic vinyl ethers such as 2-norbornen-2-yloxy groups and groups in which the vinyl ether function is connected to the spacer S or the branches of Z through an intervening hydrocarbyl structure such as 4-vinyloxybenzene and 2-vinyloxyethyl groups.

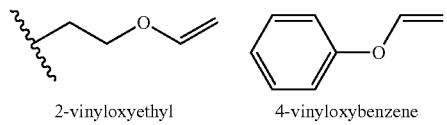

2-vinyloxyethyl     4-vinyloxybenzene

The above groups show examples of cross-linking groups, with the former also including a portion of the spacer group S.

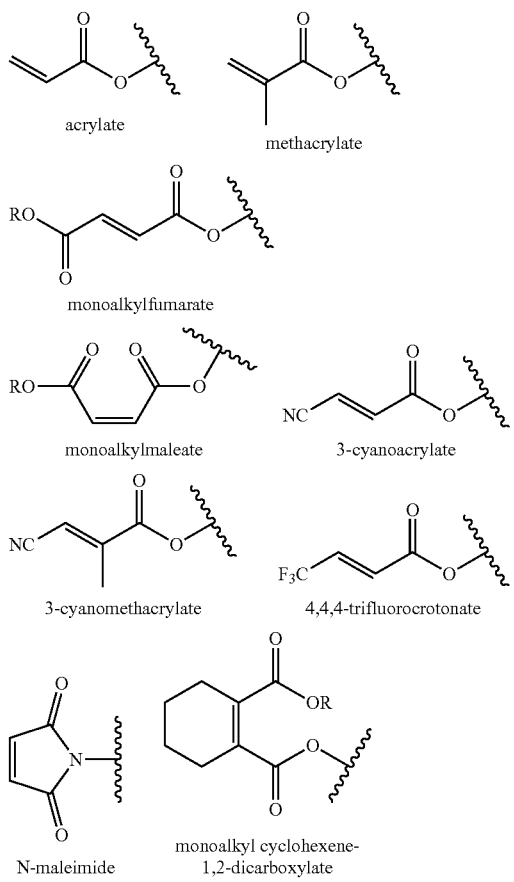

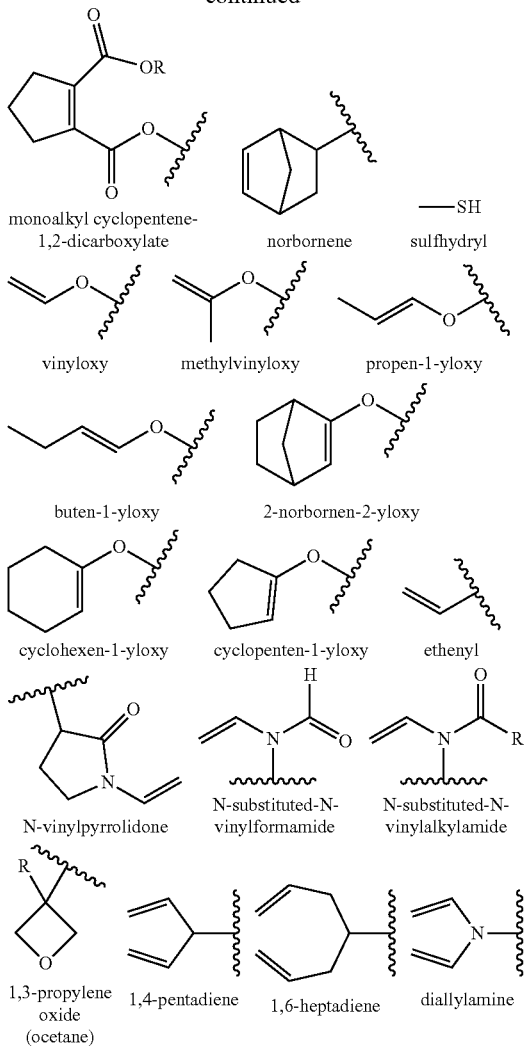

In a preferred aspect the cross-link groups are electron-poor ethylenic cross-linkable groups. Electron deficient ethylenic cross-linkable groups contain an ethylene group substituted with one or more electron withdrawing groups. The electron withdrawing group may comprise a carbonyl group and may for example be an ester or an amide. In a preferred aspect the electron deficient cross-linkable group comprises a monoalkylmaleate group, a monoalkylfumarate group, a monoarylmaleate group, a monoarylfumarate group or a maleimide group. Other examples of electron deficient crosslinking groups are acrylate groups, methacrylate groups, 4,4,4-trifluorocrotonate groups, Z- and E-3-cyanoacrylates, Z- and E-3-cyanomethacrylates, monoalkyl cyclohexene-1,2-dicarboxylates, and monoalkyl cyclopentene-1, 2-dicarboxylates.

The ligands of the invention as described above are useful for forming complexes with light emitting properties that find application for example as light emitters in OLED devices amongst other applications. The emission properties of the complex can be tailored to the intended application by varying the nature of the ligand and the metal.

The presence of cross-linkable groups B allow complexes formed from the ligands of the present invention to be deposited in layers from solution processing, then once the solvent is removed they can be fixed in place by cross-link to form a relatively insoluble network polymer. The complexes formed between the ligands of the present invention as described below and the preferred metals are soluble in common organic solvents. This is significant as the solubility of the complexes of the invention provides distinct advantages in terms of device fabrication relative to e.g. polymeric materials. In more detail, these complexes are suitable for a solution processing approach to OLED device fabrication. In outline, this involves first dissolving the complex in an organic solvent, applying the resultant solution to a substrate and then evaporating to generate a film coating on the substrate. Once the material is deposited as a film the material can be polymerised in situ. This polymerisation may be initiated by exposure to radiation, for instance ultraviolet light, which causes the cross-linkable groups of one molecule to cross-link with those in an adjacent molecule to form a network polymer. Regions of the deposited film can be masked from the initiating radiation to give zones of non-cross-linked material while zones exposed to radiation undergo polymerisation. If desired the unexposed, non-cross-linked material can be washed off to leave behind a patterned structure of cross-linked material due to the cross-linked material having negligible or reduced solubility relative to that of the monomer. Iterative cycles of solution deposition and polymerisation can be used to generate structures with complex architectures.

Sequentially deposited polymerised structures can be assembled in a side by side or stacked/layered manner. In one example, sequential deposition and polymerisation of red, green and blue emitting material in a side by side manner can be used to generate pixels for colour displays. In another example, a stack of red, green and blue emitter materials can be used to give a white light source. In another example, two or more emitter structures can be arranged in a stack to give a coloured light source.

The ability to cheaply and economically produce multi-layer devices in which adjoining layers have different highest occupied or lowest unoccupied molecular orbital (HOMO and LUMO) energy levels as well as different charge carrier mobilities is of general utility in plastic electronics. For instance, the equivalent of p-n junctions may be formed using the materials and processes of this invention and these may find utility in diodes, transistors, and photovoltaic devices. The propensity of the complexes of the invention to be photo lithographically patterned allows large arrays of plastic electronic devices of virtually any size and description to be fabricated.

Complexes according to this invention may be mixed together with a liquid crystalline host material to form layers in which the emitter cores with a high degree of directional order. This can be very advantageous from the standpoint of optimising the material properties for OLED as noted above. This directional order can be fixed in place by cross-link the components of the deposited films, for example by exposing the deposited film to radiation such as ultraviolet light. For example, linearly polarised emission uniaxial molecular orientation of the phosphor (i.e. the metal complexes of the invention) is achieved using a nematic photo-crosslinkable liquid crystal host on either a rubbed polymer surface (i.e., PEDOT, polyimide or nylon 6,6) or by photoalignment of coumarin derivatives. The nematic liquid crystal acts as a host and the organometallic material (the phosphor) acts as the emissive dopant. For multi-layer OLED capability, the host-dopant system is preferably photo-crosslinkable in which a solution deposited film can be rendered insoluble to common organic solvents after UV-curing. The resulting insolubility of the film allows layers to be solution processed on top without damaging or washing away the phosphorescent host-dopant layer below.

The potential to obtain highly ordered device structures can be exploited to generate polarised light emitting structures in which the emitter cores are aligned in the same direction and therefore emit light in the same direction. Ultimately, the properties of the materials described herein afford the possibility to fabricate 3D-displays through sequential deposition of aligned layers of uniformly aligned liquid crystalline fluid or glass, sequential polymerisation of patterned areas of each layer in turn, and sequentially washing away of unpolymerised areas of each layer in turn so as to provide light emitting structures such that the polarisation axis of light emission of each respective layer is in a different direction. For linearly polarised emission uniaxial molecular orientation of the phosphorescent emitter can be achieved using a nematic photo-crosslinkable liquid crystal host on either a rubbed polymer surface (i.e., PEDOT, polyimide or nylon 6,6) or by photoalignment of coumarin derivatives. The nematic liquid crystal acts as a host and the organometallic material (the phosphor) acts as the emissive dopant.

The materials of the present invention also possess a number of additional desirable properties that render them useful for the production of electronic devices such as OLEDs. In organic light emitting devices it is often also desirable to reduce the self-absorption of emitted light by organic luminescent materials. This self-absorption occurs because the spectral absorbance and emission bands of organic luminescent materials overlap to a greater or lesser extent in various materials. A solution to this problem well known, for instance, in the field of dye lasers is to dissolve the luminescent material in a host with that absorbs light at a shorter wavelength than the luminescent solute. If the solution is dilute, for instance one to two percent, the self-absorption of the luminescent solute is nearly completely suppressed. The facile mutual miscibility of the various compounds of this invention makes the preparation of solutions of this type very easy. The materials of the present invention therefore are useful as host materials as well as light emitting materials.

In organic light emitting device applications it is necessary that there be facile excitation energy transfer from the host material to the solute luminescent material. This is because charge carriers (electrons and holes) must be transported through the host medium to recombine to form the excitons (electrically excited molecular orbital states) that radiate light. In a mixture composed mainly of component host molecules this recombination and exciton formation will mainly occur in the host molecules. The excitation energy then needs to be transferred from the host molecules into the luminescent solute molecules. It is a requirement for this energy transfer that the spectral luminescent emission band(s) of the host material overlap the absorption band of the luminescent solute. Thus an important aspect of the invention is the preparation of mixtures of the compounds of the invention that have this spectral relationship between the constituent components. For instance, a compound which emits in the blue region of the spectrum can serve as a host for a compound which is a green light emitter. A polymer film prepared by the UV induced crosslinking of a solution of 5% blue emitter compound in green emitter compound will exhibit considerably less self-absorption of the green light emitted by the green emitter than will a film prepared by UV crosslinking of pure green emitter.

Complexes

The ligands of the present invention are useful for making both octahedral and square planar transition metal complexes. Octahedral complexes of iridium (III), osmium (II), ruthenium (II) and square planar complexes of platinum (II) are preferred.

The octahedral complexes of the invention feature a metal selected from iridium (III), osmium (II) and ruthenium (II) listed above and either one ligand of the invention and a 1,4-bidentate ligand and ancillary ligand(s) or two ligands of the invention and ancillary ligand(s). Exemplary complexes of the present invention wherein the second ligand centres of $L^1$ and $L^2$ are nitrogen, first ligand centres are $sp^2$-hybridised carbons, and the arm, of each of $L^1$ and $L^2$, optionally terminate in one or two cross-linkable groups B (and $B^1$).

The invention also relates to square planar complexes of platinum (II) two with a single ligand according to the invention of type Lb and a bidentate ancillary ligand or a pair of monodentate ancillary ligands.

Complexes according to the invention can be formed under standard conditions, for example by heating the appropriate ligand of structure La and metal salt in the appropriate solvent and then adding in the appropriate ancillary ligand. This process is shown schematically for octahedral iridium complexes and square planar platinum complexes in the Schemes below.

Scheme 1 Synthesis of Octahedral complexes

Example:

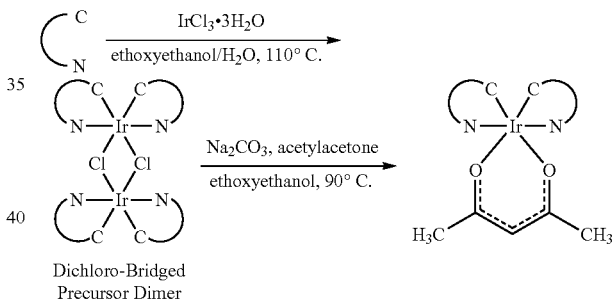

Dichloro-Bridged Precursor Dimer

The bis-heteroleptic octahedral complexes, i.e. those containing two ligands according to the present invention, form in such a manner that the second ligand centres of each ligand (a nitrogen in each case) and the metal are in substantially linear alignment. The complex thus has arms projecting along this same linear axis as can be seen in the crystal structure of Ir(4-pepe-2-ppy)$_2$(acac) shown below. This linear character and the □-stacking interaction potential provided by the aromatic rings in the ligand arms allows the complexes of the invention to align with liquid crystalline host materials and thus deliver the possibility of making emitter layers (phosphor layers) with molecular aligned emitter cores and anisotropic emission properties.

Scheme 2 Synthesis of Square Planer complexes

Example:

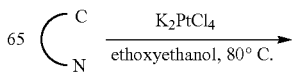

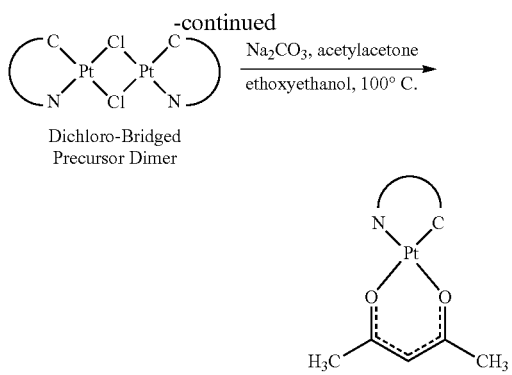

Dichloro-Bridged Precursor Dimer

While the present invention has been described with reference to ligands comprising at least one arm of the structure:

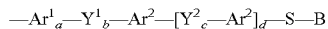

and complexes comprising said ligands, it will be appreciated that during synthesis several intermediates will be produced. In particular the ligands may be produced with one or two arms of the structure:

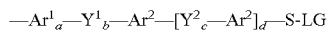

Wherein LG is a leaving group, such as a hydroxy group (—OH), a halide (—Cl or —Br or —I), a sulfonate ester (such as a -mesylate or -tosylate), a carboxylate, phenoxide or any other conventional leaving group as would be known in the art.

Producing complexes from ligands including cross-linkable groups can cause complication during synthesis. In particular, reactions to form the complexes are often performed at increased temperature. Cross-linkable groups are often unstable at increased temperature. Therefore, it may be advantageous to form the complexes using ligands comprising one or more arms of the above intermediate structure and then add the cross-linking group to the already metallated ligand complex by reaction with the leaving group.

Examples of addition of the cross-linking groups both before and after metallation are provided in the non-limiting examples below.

SYNTHETIC EXAMPLES

The compounds and complexes of the present invention may be synthesised by common techniques in organic synthesis and organometallic chemistry well known to those of ordinary skill in the art. Illustrative examples of how these compounds can be synthesised are presented below. As can be appreciated, the nature of these materials allows a modular approach to synthesis to be adopted. The examples provided below are by way of example only and in no way limit the scope of the invention.

Scheme 1: Synthesis of Bis-Heteroleptic Cross-linkable Iridium Complex Ir(4-dpe-2-ppy)$_2$(acac)

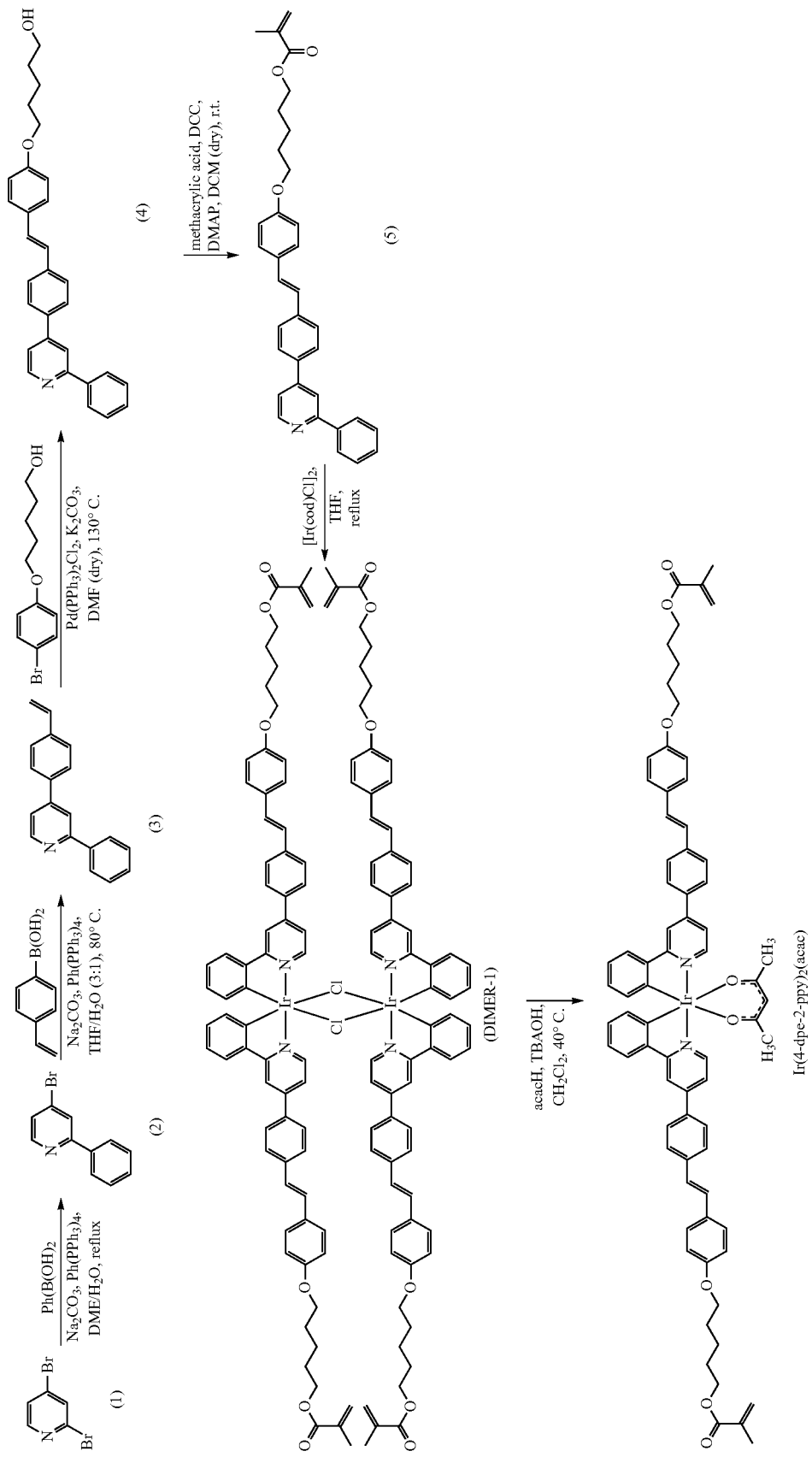

Suzuki coupling of 4-bromo-2-phenylpyridine (1) with phenylboronic acid, using Pd(PPh$_3$)$_4$ as the catalyst, gave good selectivity at the pyridine 2-position and afforded compound (2) in good yield. This allowed a remaining Ar—Br bond to be utilised in a second Suzuki coupling using (4-vinylphenyl)boronic acid to afford compound (3). Heck coupling using Pd(PPh$_3$)$_2$Cl$_2$ as the catalyst at 130° C. in DMF with 5-(4-bromophenoxy)pentan-1-ol yielded compound (4), which was esterified with methacrylic acid by a Steglich esterification to afford (E)-5-(4-(4-(2-phenylpyridin-4-yl)styryl)phenoxy)pentyl methacrylate (5). Subsequent cyclometalation using bis(1,5-cyclooctadiene) diiridium(I) dichloride ([Ir(cod)Cl]$_2$) as the iridium source in refluxing THF (dry and degassed) afforded DIMER-1 that was converted to the cross-linkable bis-heteroleptic acac phosphor Ir(4-dpe-2-ppy)$_2$(acac) using acetylacetone with tetrabutylammonium hydroxide in DCM at 40° C.

4-bromo-2-phenylpyridine (2)

2,4-Dibromopyridine (compound 1, 4.35 g, 0.0184 mol), phenylboronic acid (2.24 g, 0.0184 mol), Na$_2$CO$_3$ (5.84 g, 0.0551 mol), dimethoxyethane (50 mL) and water (20 mL) were all added to a 3-neck round bottomed flask. The system was degassed with the aid of two freeze-pump-thaw cycles using nitrogen as the inert gas. Subsequently, Pd(PPh$_3$)$_4$ (1.06 g, 0.92 mmol) was added and the reaction mixture was again degassed by one freeze-pump-thaw cycle. The reaction mixture was heated under reflux for 2 days and then poured into a separating funnel. Work-up was conducted using ethyl acetate (200 mL) and the organic extract washed with water (200 mL), dried (MgSO$_4$) and filtered. The filtrate was concentrated under reduced pressure and the crude product was purified by column chromatography (dry loaded, silica gel, 100% DCM) to yield a pale-yellow oil (2.85 g, 66.3%).

2-phenyl-4-(4-vinylphenyl)pyridine (3)

4-Bromo-2-phenylpyridine (compound 2, 2.00 g, 0.0085 mol), (4-vinylphenyl)boronic acid (1.52 g, 0.0103 mol), Na$_2$CO$_3$ (2.72 g, 0.0256 mol), tetrahydrofuran (30 mL) and water (10 mL) were all added to a 3-neck round bottomed flask. The system was degassed with the aid of two freeze-pump-thaw cycles using nitrogen as the inert gas. Subsequently, Pd(PPh$_3$)$_4$ (0.99 g, 0.85 mmol) was added and the reaction mixture was again degassed by one freeze-pump-thaw cycle. The reaction mixture was heated under reflux for 2 days and then poured into a separating funnel. Work-up was conducted using diethyl ether (2×150 mL) and the organic extracts washed with water (2×200 mL), dried (MgSO$_4$) and filtered. The filtrate was concentrated under reduced pressure and the crude product was purified by column chromatography (dry loaded, silica gel, 100% DCM) to yield a powder.

(E)-5-(4-(4-(2-phenylpyridin-4-yl)styryl)phenoxy)pentan-1-ol (4)

2-Phenyl-4-(4-vinylphenyl)pyridine (compound 3, 2.00 g, 0.0078 mol), 5-(4-bromophenoxy)pentan-1-ol (3.02 g, 0.0117 mol), K$_2$CO$_3$ (1.07 g, 0.0078 mol) and dry DMF (50 mL) were all added to a 3-neck round bottomed flask. The system was degassed with the aid of two freeze-pump-thaw cycles using nitrogen as the inert gas. Subsequently, Pd(PPh$_3$)$_2$Cl$_2$ (0.27 g, 0.39 mmol) was added and the reaction mixture was heated at 130° C. for 24 h. The reaction mixture was then poured into a separating funnel, DCM was added (200 mL), followed by water (200 mL), the aqueous layer extracted with more DCM (100 mL) and the combined organics were washed with water (200 mL), dried (MgSO$_4$) and filtered. After evaporating the filtrate to dryness under reduced pressure, the crude product was purified by column chromatography (dry loaded, silica gel, 30% ethyl acetate in hexanes) to yield a powder.

(E)-5-(4-(4-(2-phenylpyridin-4-yl)styryl)phenoxy)pentyl methacrylate (5)

DCC (0.95 g, 0.0046 mol) was added portion wise to a solution of compound 4 (1.00 g, 0.0023 mol), methacrylic acid (0.40 g, 0.0046 mol) and DMAP (0.28 g, 0.0023 mol) in dry CH$_2$Cl$_2$ (25 mL) at room temperature under a nitrogen atmosphere. The reaction mixture was stirred for 24 h and the formed DCU was filtered and CH$_2$Cl$_2$ was removed under reduced pressure. The resulting residue was purified by column chromatography (wet loaded, silica gel, 100% DCM) to yield a powder.

Ir(4-dpe-2-ppy)$_2$(acac)

A solution of compound 5 (0.50 g, 0.99 mmol) in dry THF (20 ml) was degassed by 3×freeze-pump-thaw cycles and [Ir(cod)Cl]$_2$ (0.32 g, 0.48 mmol) was added. The reaction mixture was heated under reflux for 2 days, cooled to room temperature and the formed precipitate filtered. After drying under vacuum DIMER-1 was obtained as a solid. Subsequently, a solution of DIMER-1 (0.30 g, 0.12 mmol), TBAOH (30-hydrate, 0.97 g, 1.22 mmol) and acetylacetone (5 ml) in DCM (50 ml), was heated to 40° C. overnight. The reaction mixture was then poured into a separating funnel, DCM was added (100 mL), followed by water (150 mL), the aqueous layer extracted with more DCM (100 mL) and the combined organics were washed with water (200 mL), dried (MgSO$_4$) and filtered. After evaporating the filtrate to dryness under reduced pressure, the crude product was purified by column chromatography (dry loaded, silica gel, 50% DCM in hexanes) to yield a powder.

Scheme 2: Synthesis of Bis-Heteroleptic
Cross-linkable Iridium Complex
Ir(4-durph-2-pyrpy)$_2$(acac)
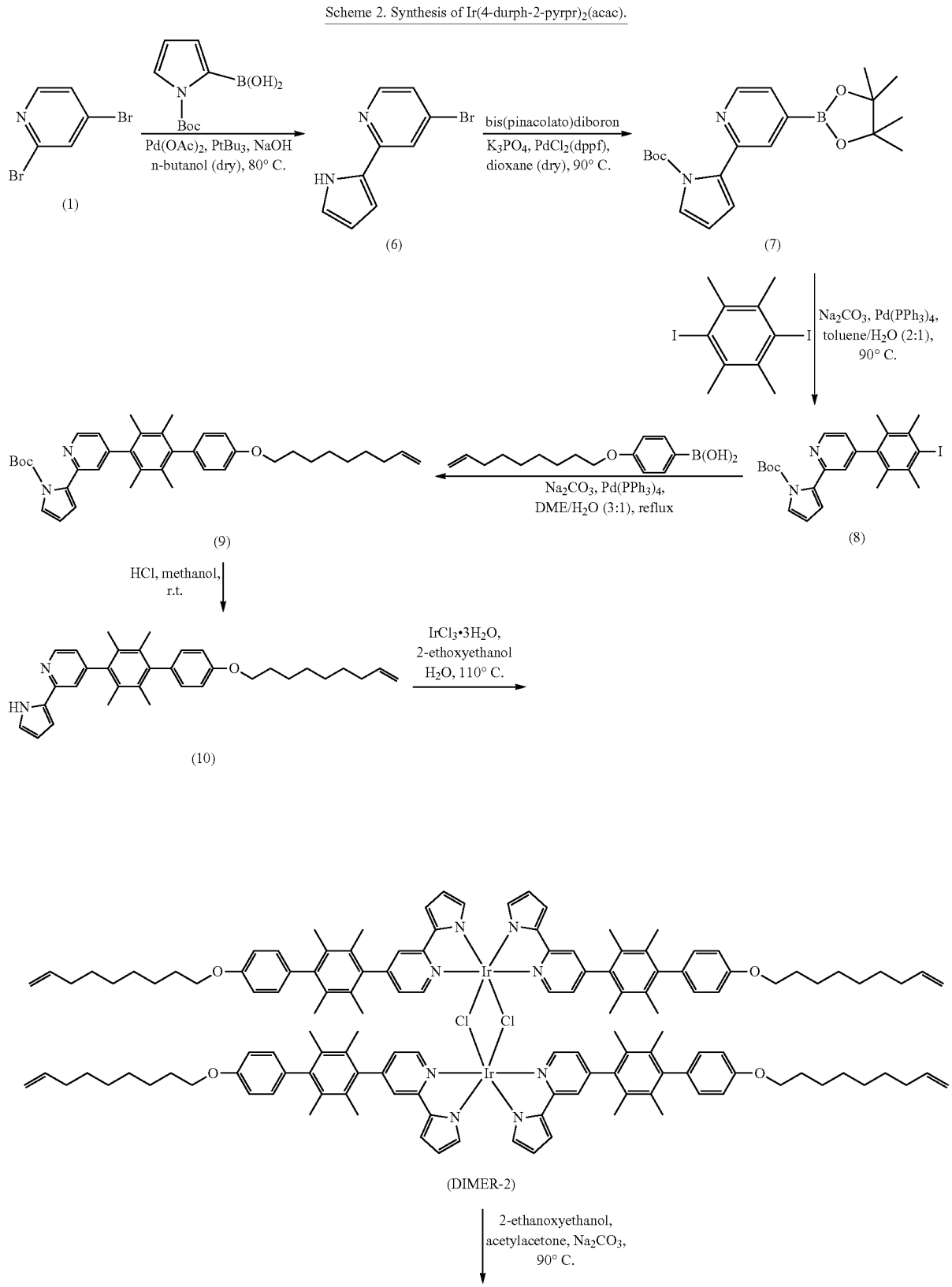

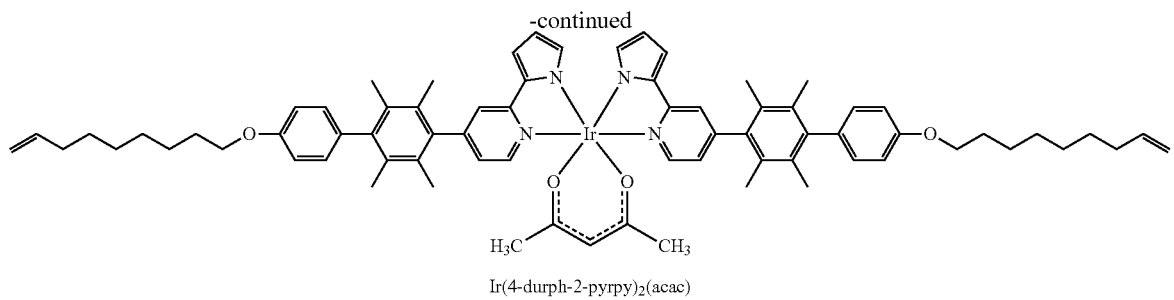

Ir(4-durph-2-pyrpy)₂(acac)

The Suzuki coupling reaction of 4-bromo-2-phenylpyridine (1) with N-Boc-2-pyrroleboronic acid, using Pd(OAc)₂ as the catalyst, was carried out in a glove box due to the air sensitivity of PtBu₃, and afforded 4-bromo-2-(N-Boc-pyrrol-2-yl)pyridine (6) with good selectivity. This allowed the remaining Ar—Br bond to be utilised and converted into a boronic ester functional group (7) and mono-Suzuki coupled to 1,4-diiododurene to yield compound (8). The cross-linking group was attached to compound (8) via Suzuki coupling reaction with (4-(non-8-en-1-yloxy)phenyl)boronic acid to yield compound (9). Boc deprotection to give (10) and subsequent cyclometalation using IrCl₃.3H₂O in 2-ethoxyethanol/H₂O at 110° C. afforded DIMER-2 that was converted to the cross-linkable bis-heteroleptic acac phosphor Ir(4-durph-2-pyrpy)₂(acac) using acetylacetone and sodium carbonate in 2-ethoxyethanol at 90° C.

Scheme 3: Synthesis of Square Planar Cross-linkable Platinum Complex Pt(3-ph-4-ph)-(2-ppy)(acac)

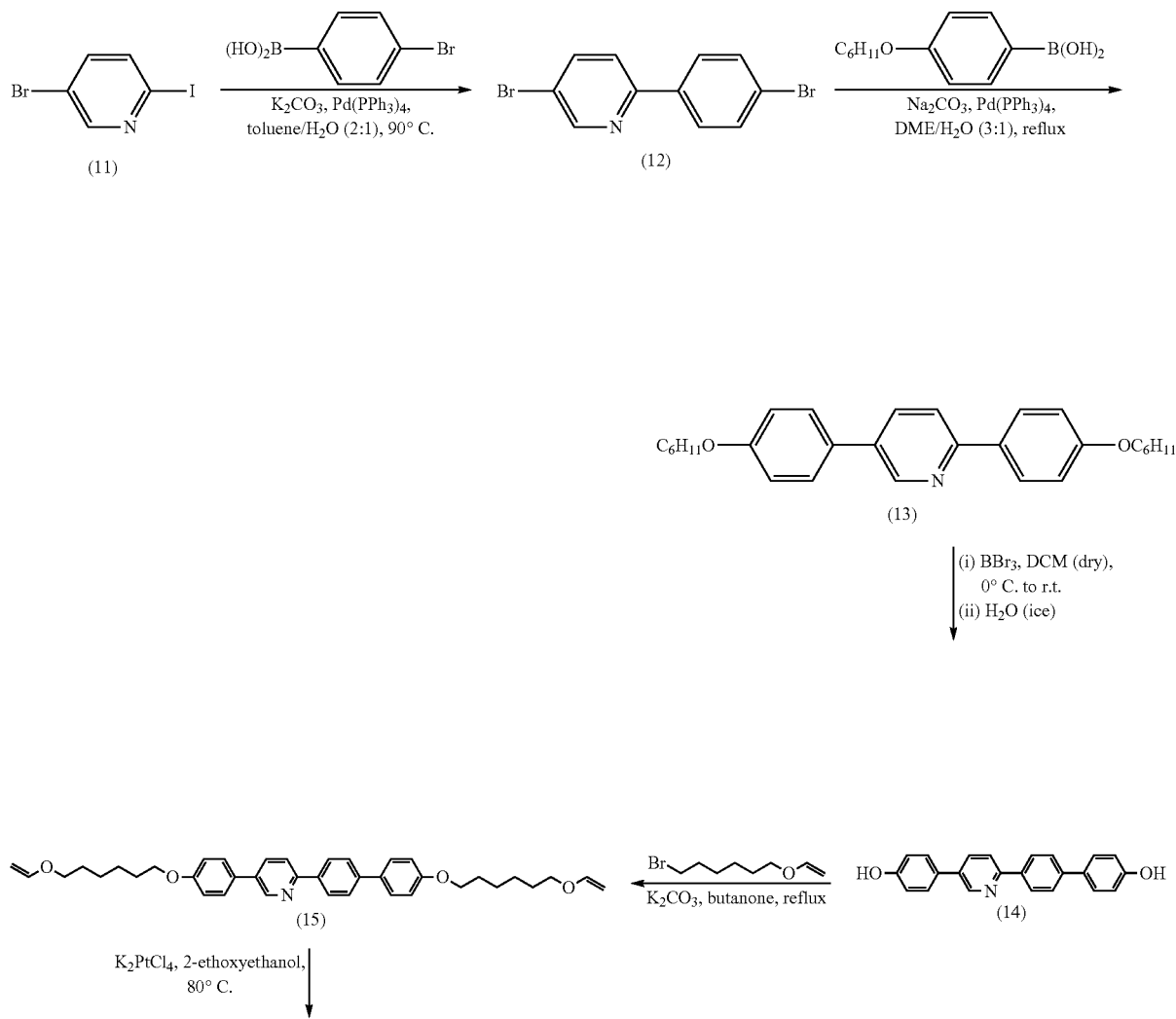

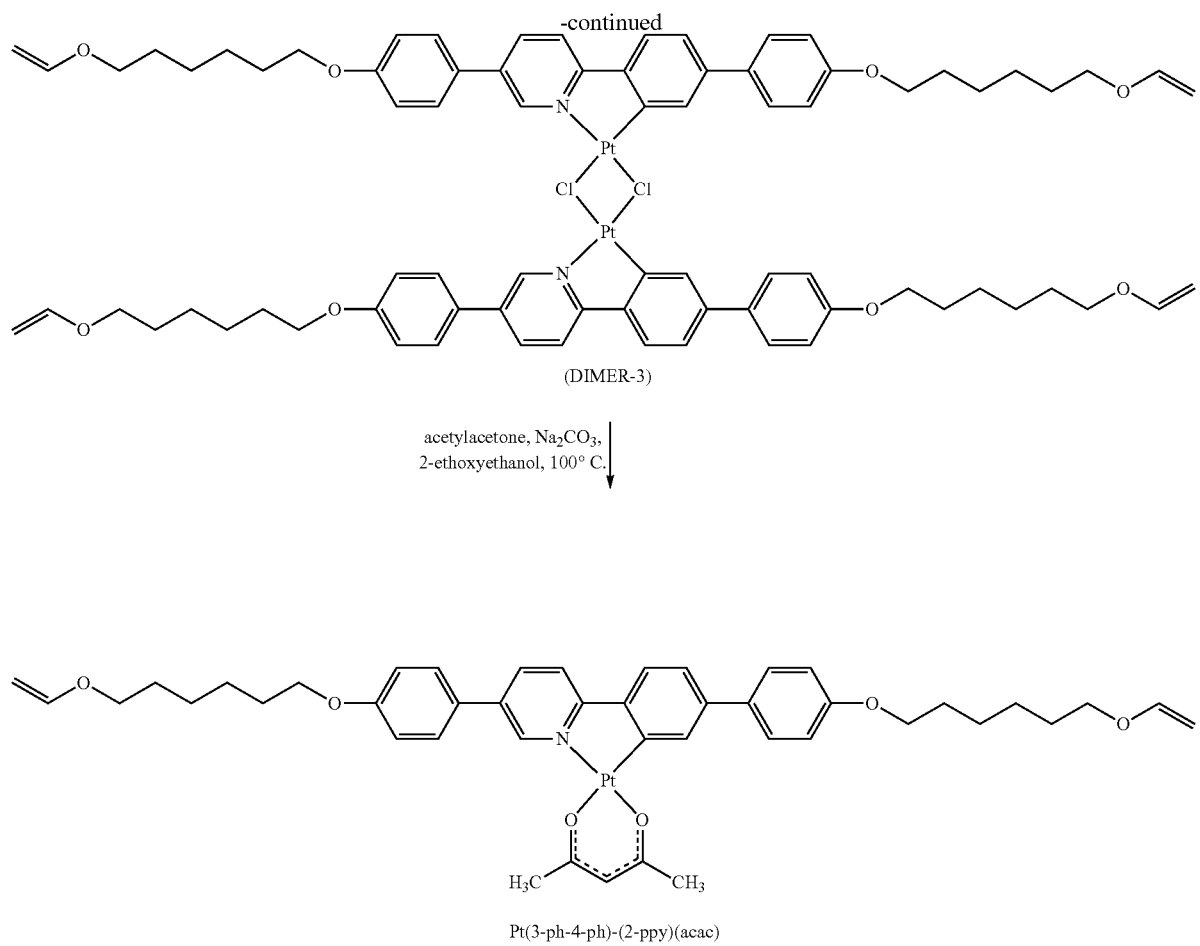

Suzuki coupling reaction of 5-bromo-2-iodopyridine (11) with (4-bromophenyl)boronic acid, using Pd(PPh₃)₄ as the catalyst, afforded compound (12) in moderate yield. 5-Bromo-2-(4-bromophenyl)pyridine (12) was then converted to compound (13) by Suzuki coupling with (4-(octyloxy)phenyl)boronic acid, which was followed by octyloxy deprotection using BBr₃ to afford the corresponding bis-phenol (14). The cross-linking group was attached to compound (14) via Williamson-ether reaction in refluxing butanone using potassium carbonate as the base with 8-bromo-1-vinyloxy octane to yield compound (15). Subsequent cyclometalation of 15 using K₂PtCl₄ in 2-ethoxyethanol at 80° C. afforded DIMER-3 that was converted to the cross-linkable acac phosphor Pt(3-ph-4-ph)-(2-ppy)(acac) using acetylacetone and sodium carbonate in 2-ethoxyethanol at 100° C.

Scheme 4: Synthesis of Bis-Heteroleptic Non-Cross-Linkable Iridium Complex's Ir(4-p-2-ppy)₂(acac) and Ir(4-bp-2-ppy)₂(acac)

Scheme 4. Synthesis of phenyl and biphenyl substituted 2-phenyl pyridine ligands and organometallic complexes (Ir(4-p-2-ppy)₂(acac) and (Ir(4-bp-2-ppy)₂(acac)) featuring these ligands.

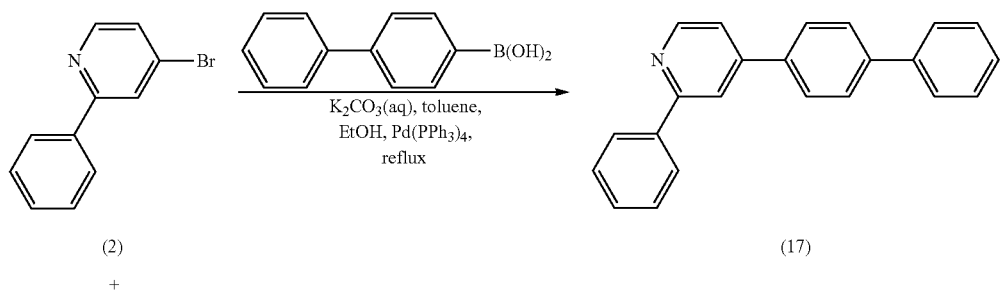

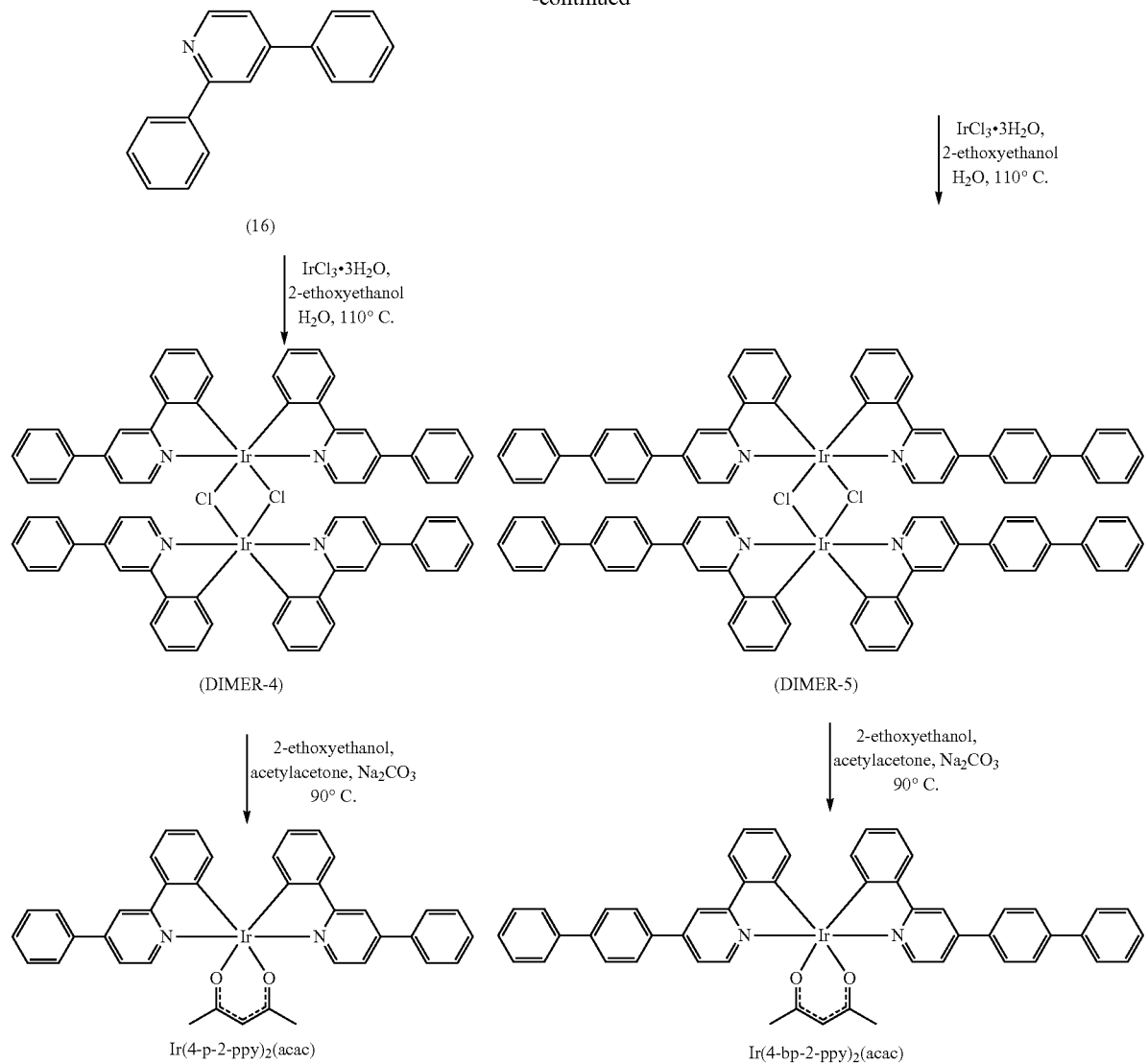

Scheme 4 demonstrates the synthesis of the central portion of the ligands to which spacers can be attached to arrive at the ligands of the invention as defined in the claims.

4-Bromo-2-phenylpyridine (2) was prepared according to the previous procedure with 0.54 g of 2,4-diphenylpyridine (16) obtained as a by-product. Suzuki coupling reaction of 4-bromo-2-phenylpyridine (2) with 1,1'-biphenyl]-4-ylboronic acid, using Pd(PPh₃)₄ as the catalyst, afforded compound (17) in good yield. Subsequent cyclometalation of compound (17) using IrCl₃.3H₂O in 2-ethoxyethanol/H₂O at 110° C. afforded DIMER-5 that was converted to the bis-heteroleptic acac phosphor Ir(4-bp-2-ppy)₂(acac) using acetylacetone and sodium carbonate in 2-ethoxyethanol at 90° C. Finally, cyclometalation of compound (16) using IrCl₃.3H₂O afforded DIMER-4 that was converted to the bis-heteroleptic acac phosphor Ir(4-p-2-ppy)₂(acac) using acetylacetone and sodium carbonate in 2-ethoxyethanol at 90° C.

4-([1,1'-Biphenyl]-4-yl)-2-phenyl pyridine (17)

1,1'-Biphenyl-4-ylboronic acid (0.99 g, 0.0050 mol), 4-bromo-2-phenylpyridine (0.90 g, 0.0038 mol), K₂CO₃ (2.65 g, 0.0192 mol), toluene (30 ml) ethanol (5 ml) and water (15 ml) were all added to a 3-neck round bottomed flask and the system was evacuated, with the aid of a vacuum pump, and filled with nitrogen 3 times. Subsequently, Pd(PPh₃)₄ (0.22 g, 0.19 mmol) was added and the reaction mixture was stirred under reflux overnight. The reaction mixture was poured into a separating funnel, in which more water (50 ml) and toluene (50 ml) were both added, the water layer washed with toluene (20 ml) and the combined organic layers washed with water (50 ml), dried (MgSO₄) and filtered. The crude product was purified by column chromatography (dry loaded, silica gel, 100% DCM to 5% ethanol/DCM) to yield a white powder (0.59 g, 50%). ¹H-NMR (400 MHz, CDCl₃): δ (ppm) 8.76 (1H, dd, J=5.0 and 0.6 Hz), 8.06-8.08 (2 H, m), 7.99 (1 H, dd, J=1.6 and 0.8 Hz), 7.80 (2 H, d, J=8.4 Hz), 7.75 (2 H, d, J=8.8 Hz), 7.66 (2 H, m), 7.46 (7 H, m).

Ir(4-p-2-ppy)₂(acac)

A suspension of compound 16 (0.54 g, 2.33 mmol) in 2-ethoxyethanol (20 ml) and water (7 ml) was purged with nitrogen and IrCl₃·3H₂O (0.41 g, 1.13 mmol) was added. The reaction mixture was heated to 110° C. overnight (20 h), cooled to room temperature and precipitated with water (40 ml). The precipitate was filtered, washed with water and dried (dissolved in DCM with MgSO₄). After evaporating the solvent using a rotary evaporator and drying under vacuum a red powder (DIMER-4) was obtained (0.56 g, 71.8%). Subsequently, a reaction mixture containing the DIMER-4 (0.54 g, 0.39 mmol), Na₂CO₃ (0.60 g, 5.66 mmol) and acetylacetone (5 ml) in 2-ethoxyethanol (50 ml), was heated to 90° C. overnight. The reaction mixture was cooled to room temperature and precipitated with water (50 ml), filtered and dried (dissolved in DCM with MgSO₄). The crude product was purified by column chromatography (dry loaded, silica gel, 50% DCM/hexanes) to yield a yellow-orange powder (0.17 g, 28.8%). ¹H-NMR (400 MHz, CDCl₃): δ (ppm) 8.56 (2 H, d, J=6.0 Hz), 8.06 (2 H, d, J=2.0 Hz), 7.80-7.81 (4 H, m), 7.65 (2 H, dd, J=8.0 and 1.2 Hz), 7.48-7.59 (6H, m), 7.38 (2 H, dd, J=6.0 and 2.0 Hz), 6.84 (2 H, td, J=7.2 and 1.2 Hz), 6.73 (2 H, td, J=7.2 and 1.2 Hz), 6.38 (2H, dd, J=7.6 and 0.8 Hz), 5.26 (1H, s), 1.83 (6H, s), ASAP-MS: 753.2 ([M+1]⁺).

Ir(4-bp-2-ppy)₂(acac)

A suspension of compound 17 (0.56 g, 1.82 mmol) in 2-ethoxyethanol (35 ml) and water (10 ml) was purged with nitrogen and IrCl₃·3H₂O (0.32 g, 0.89 mmol) was added. The reaction mixture was heated to 110° C. overnight (20 h), cooled to room temperature and precipitated with water (50 ml). The precipitate was filtered, washed with water and dried (dissolved in DCM with MgSO₄). After drying under vacuum a red powder (DIMER-5) was obtained (0.75 g, 100%). Subsequently, a reaction mixture containing the DIMER-5 (0.75 g, 0.45 mmol), Na₂CO₃ (0.47 g, 4.43 mmol) and acetylacetone (5 ml) in 2-ethoxyethanol (50 ml), was heated to 90° C. overnight. The reaction mixture was cooled to room temperature and precipitated with water (50 ml), filtered and dried (dissolved in DCM with MgSO₄). The crude product was purified by column chromatography (dry loaded, silica gel, 50% DCM/hexanes to 100% DCM) to yield an orange powder (0.33 g, 40.7%). ASAP-MS: 905.3 ([M+1]⁺).

Scheme 5: Synthesis of Bis-Heteroleptic Cross-Linkable Iridium Complex Ir(4-dpe-2-ppy)₂(acac) (Cross-Linking Groups Added after Metalation)

Scheme 5. Example synthesis of Ir(4-dpe-2-ppy)₂(acac) wherein the cross-linking groups are added after metalation.

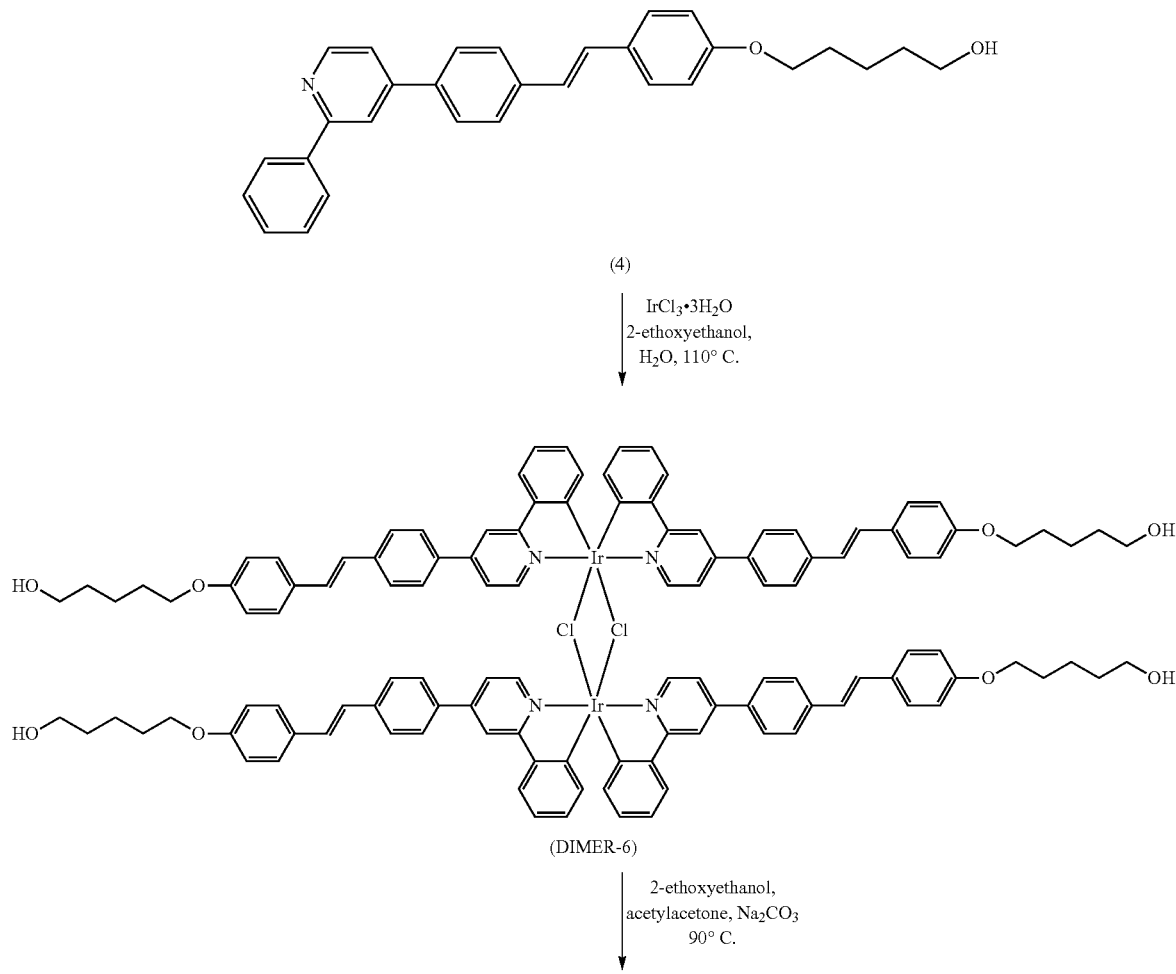

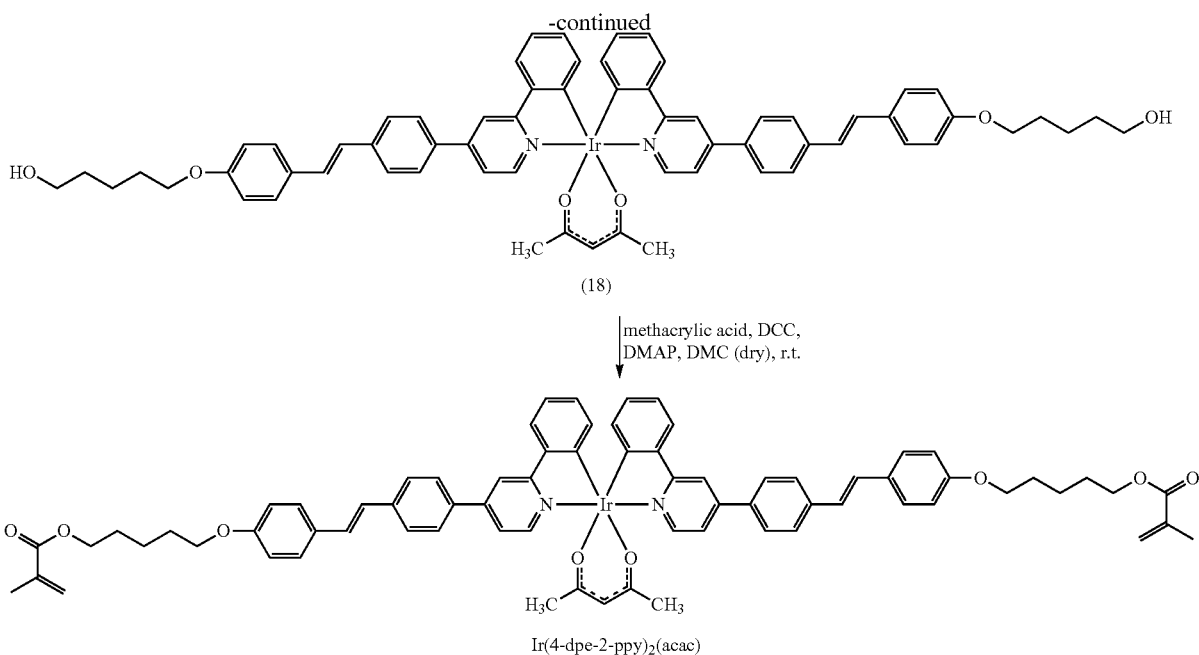
Ir(4-dpe-2-ppy)₂(acac)
Examples of Platinum Complexes
The following structures provide specific embodiments of square planar platinum complexes according to the invention.
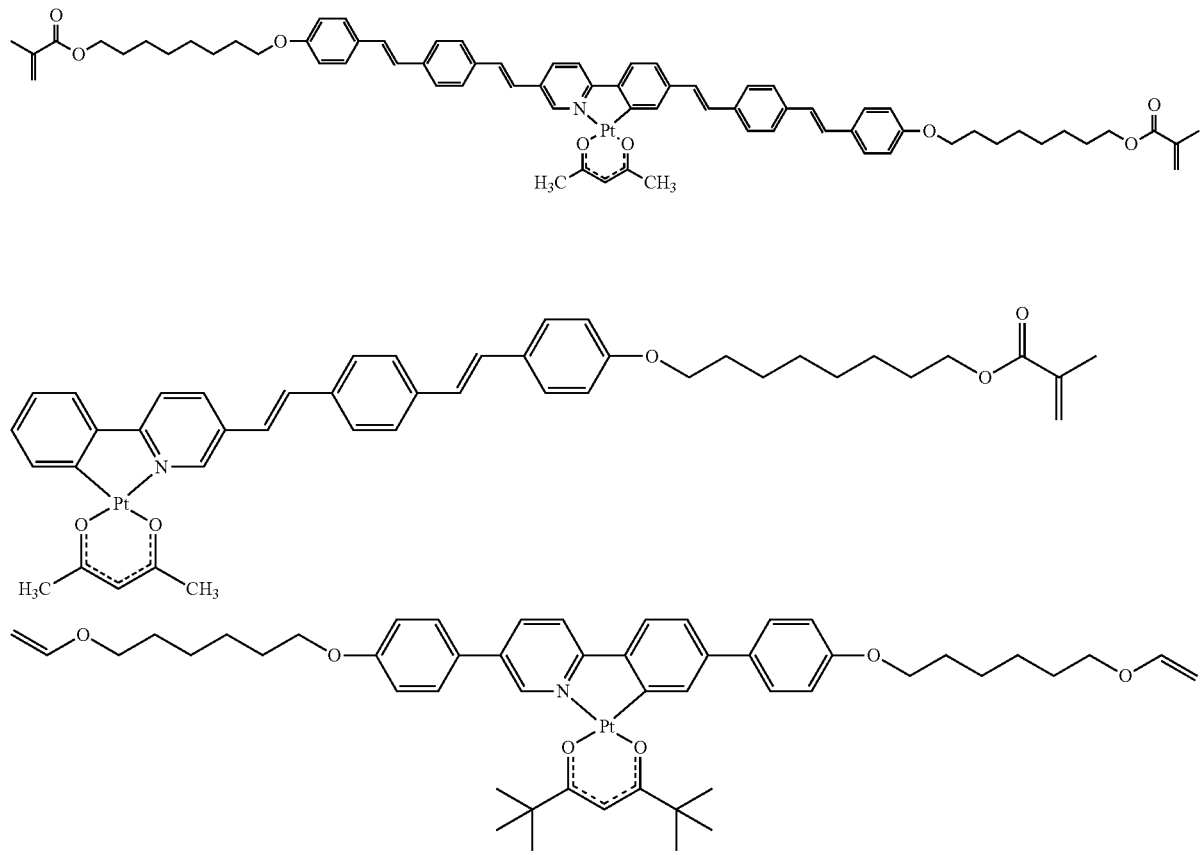

-continued
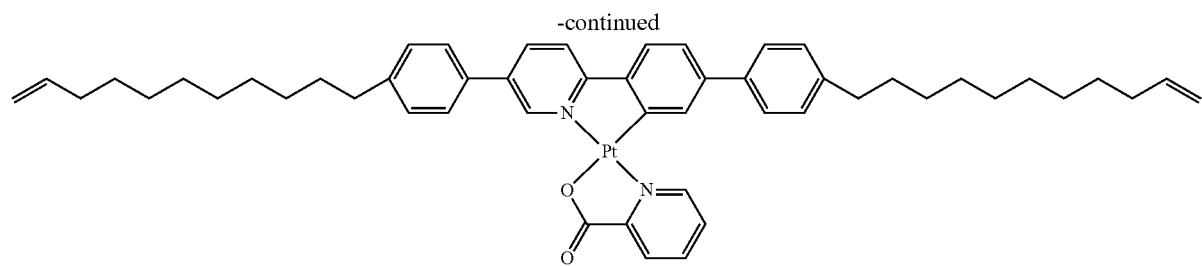
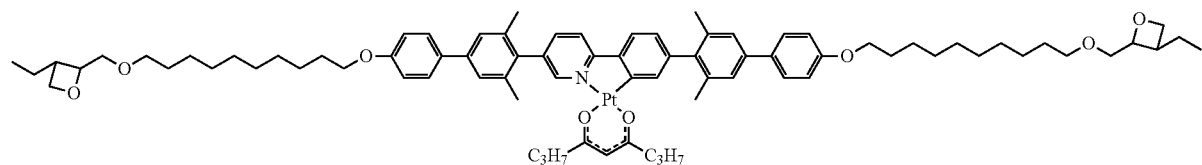
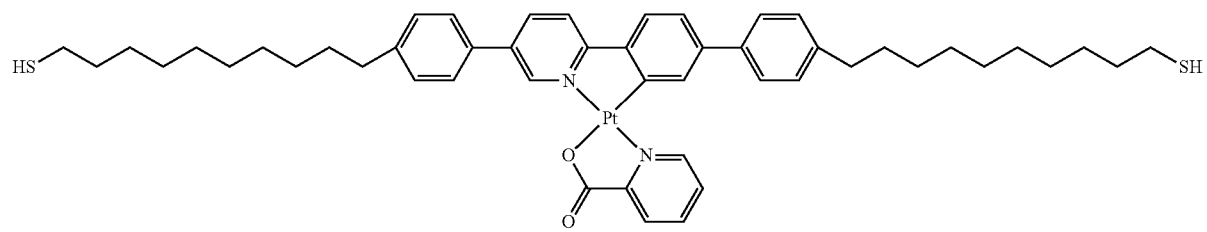
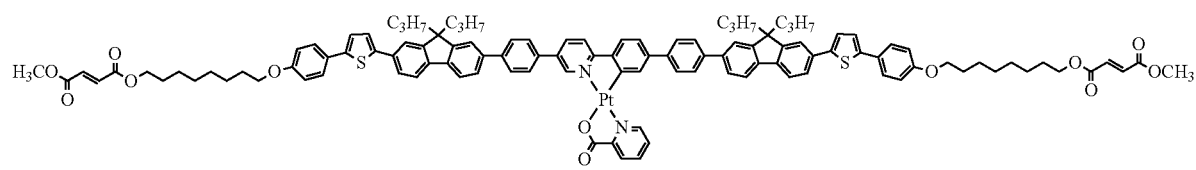
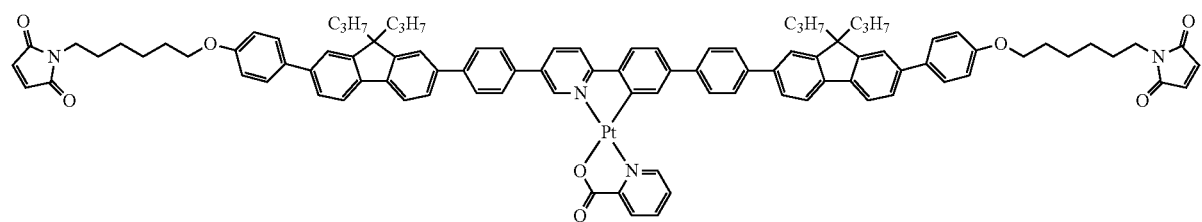
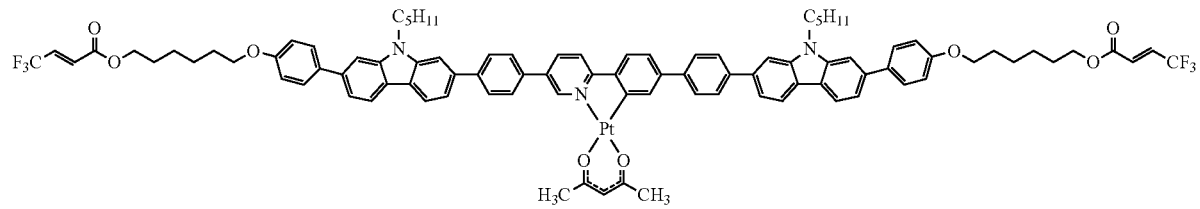
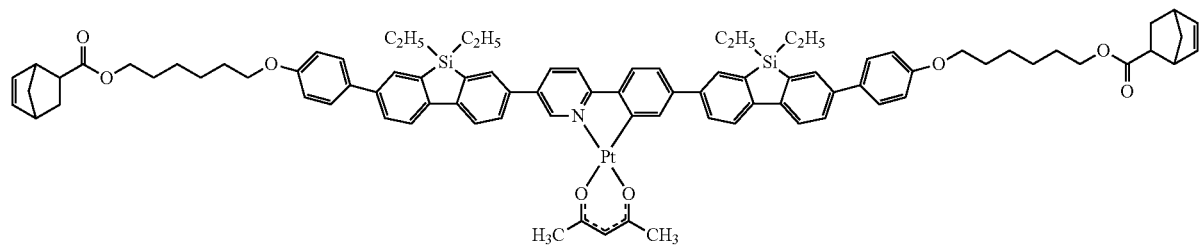

Examples of Octahedral Iridium Complexes
The following structures are examples of bis-heteroleptic octahedral complexes of the invention:
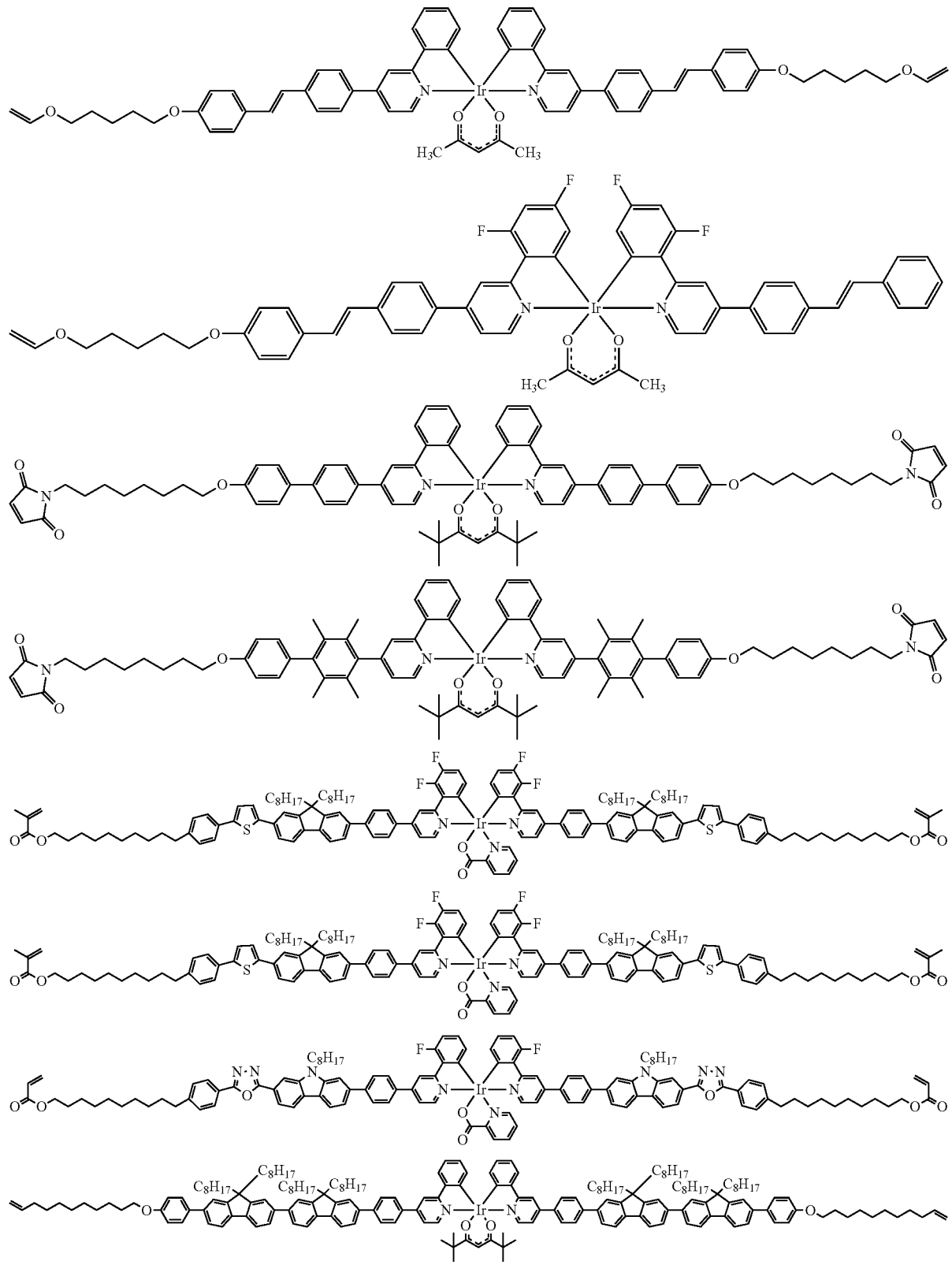

-continued
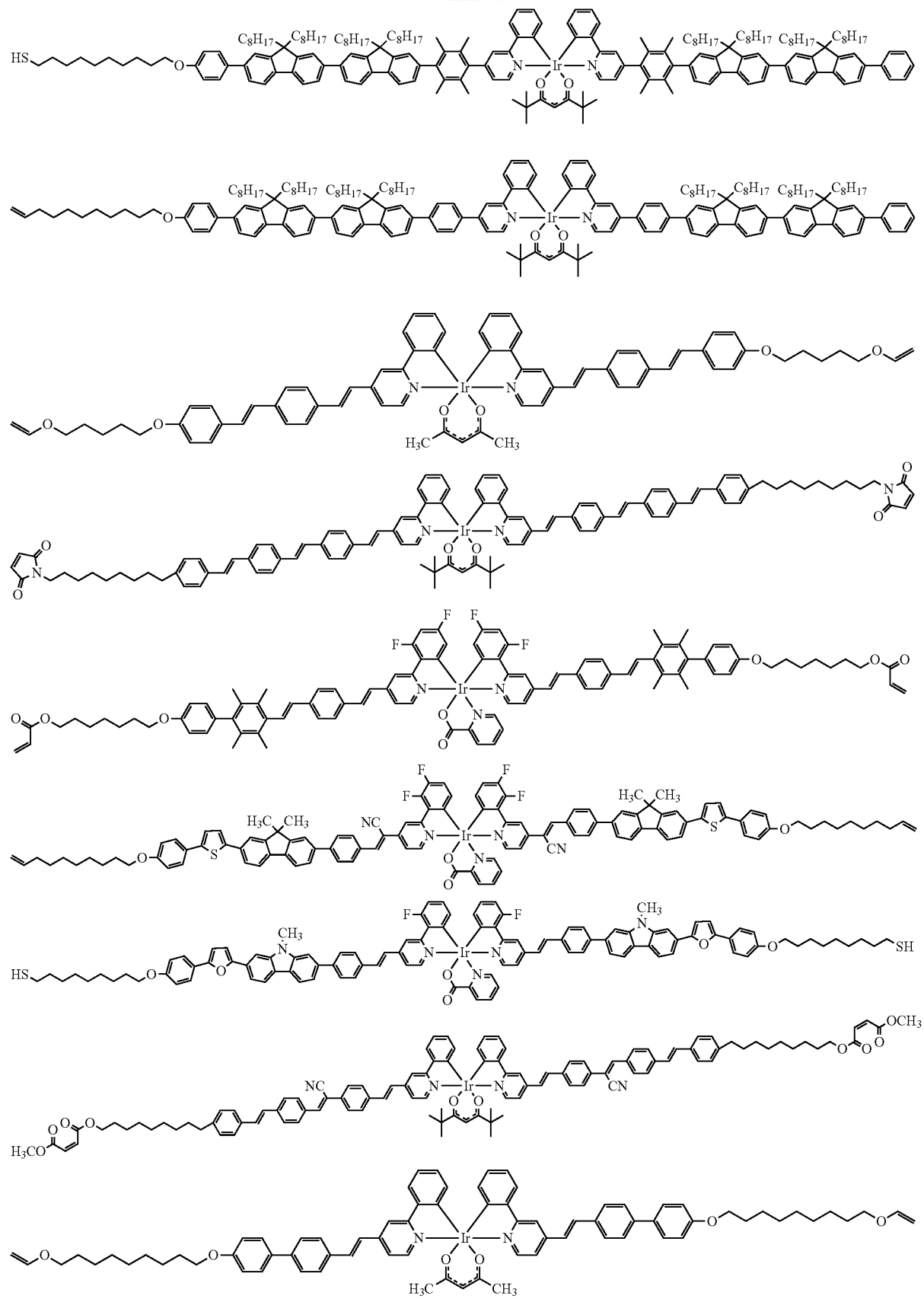

Although preferred embodiments of the invention have been described herein in detail, it will be understood by those skilled in the art that variations may be made thereto without departing from the scope of the invention or of the appended claims.

The invention claimed is:

1. A 1,4-bidentate ligand comprising first and second ligand centres,
wherein the first ligand centre is an $sp^2$-hybridised carbon or a nitrogen atom;
wherein the second ligand centre is a nitrogen atom in a five- or six-membered aromatic or hetero-aromatic ring, said ring having a substantially linear substituent $T^1$ meta or para to the nitrogen atom;
wherein $T^1$ has the formula 1:

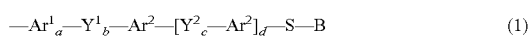

and wherein $T^1$ is attached to the ring by $X^1$, wherein $X^1$ is a bond, a methylene group, a substituted methylene group, an oxygen atom or a sulphur atom,
wherein each $Ar^1$ and $Ar^2$ are independently selected from the group of $C_6$ to $C_{20}$ aromatic and $C_4$ to $C_{20}$ heteroaromatic groups,
wherein $Y^1$ and each $Y^2$ is independently an optionally substituted $C_2$ or acetonitrile trans double-bond linking moiety,
wherein a is 0, 1, 2 or 3,
wherein b is 0, 1 or 2,
wherein each c is independently 0, 1 or 2,
wherein d is 0, 1, 2, 3 or 4,
S is a flexible spacer, and
B represents a moiety having one or more cross-linkable functionalities;
wherein the 1,4-bidentate ligand is coordinated to iridium (III), platinum (II), osmium (II) or ruthenium (II) in a complex.

2. The 1,4-bidentate ligand of claim 1, wherein b is 1 or 2.

3. The 1,4-bidentate ligand of claim 1, wherein each $Ar^1$ and $Ar^2$ are aromatic diradicals independently selected from the group consisting of 1,4-phenylene, naphthalene-1,4-diyl, naphthalene-2,6-diyl, perylene-3,10-diyl, pyrene-2,7-diyl, fluorene-2,7-diyl, fluorene-3,6-diyl, 9,9-dialkylfluorene-2,7-diyl, 9,9-dialkylfluorene-3,6-diyl, 9-(1'-alkylidiene)fluorene-2,7-diyl, 2,5-dialkoxybenzene-1,4-diyl, m-xylene, p-xylene, durene,
and/or
heteroaromatic diradicals independently selected from the group consisting of benzo[1,2-b:4,5-b']bis[1]benzothiophene-3,9-diyl, dibenzothiophene-3,7-diyl, [1]benzothieno[3,2-b][1]benzothiophene-2,7-diyl, 1,3,4-oxadiazole-2,5-diyl, 1,3,4-thiadiazole-2,5-diyl, 2,1,3-benzothiadiazole-4,7-diyl, 2,2'-dithiophene-5,5'-diyl, 4,7-dithien-2-yl-2,1,3-benzothiazole-5',5"-diyl, 4-alkyl-1,2,4-triazole-3,5-diyl, 4-thien-2-yl-2,1,3-benzothiazole-7,5'-diyl, 5,5-dioxodibenzothiophene-3,7-diyl, 5,11-dialkylindolo[3,2-b]carbazole-3,9-diyl, 5,11-dihydroindolo[3,2-b]carbazole-2,8-diyl, 9-alkylcarbazole-2,7-diyl, 9-alkylcarbazole-3,6-diyl, benzo[1,2-b:4,5-b']dithiophene-2,6-diyl, benzo[1,2-b:5,4-b']dithiophene-2,6-diyl, benzo[1,2-d:4,5-d']bisoxazole-2,6-diyl, benzo[1,2-d:5,4-d']bisoxazole-2,6-diyl, dithieno[3,2-b:2',3'-d]thiophene-2,6-diyl, imidazo[4,5-d]imidazole-2,5-diyl, oxazolo-2,5-diyl, oxazolo[4,5-d]oxazole-2,5-diyl, oxazolo[5,4-d]oxazole-2,5-diyl, pyridine-2,5-diyl, pyrimidine-2,5-diyl, 5,5-dialkyl-5H-dibenzo[b,d]silole, pyridine-2,5-diyl, pyrimidine-2,5-diyl, thiazolo[4,5-d]oxazole-2,5-diyl, thiazolo[4,5-d]thiazole-2,5-diyl, thiazolo[5,4-d]oxazole-2,5-diyl, thiazolo[5,4-d]thiazole-2,5-diyl, thieno[3,2-b]thiophene-2,5-diyl, thiophene-2,5-diyl, furan-2,5-diyl and 1,2,4,5-tetrazine-3,6-diyl.

4. The 1,4-bidentate ligand of claim 1, wherein S has the formula (2):

wherein $S^1$ is a straight chain or branched $C_4$-$C_{14}$ alkyl group, wherein from 1 to 10 $CH_2$ groups are optionally each replaced by an oxygen, provided that no acetal, ketal, peroxide or vinyl ether is present in the S group, and wherein each K is independently selected from a bond, or an ether, ester or carbonate linkage.

5. The 1,4-bidentate ligand of claim 4, wherein $S^1$ is a linear C7 alkyl chain and/or wherein B is methacrylate.

6. The 1,4-bidentate ligand of claim 1, wherein B is of the formula (3) or the formula (4):

wherein $B^1$ is a cross-linkable functionality selected from the group consisting of ethylenic, diene, thiol and oxetane cross-linkable groups,
wherein Z is a straight-chain $C_1$-$C_{12}$ alkyl, $C_1$-$C_{12}$ haloalkyl, $C_3$-$C_8$ cycloalkyl, $C_6$-$C_{16}$ aryl or $C_4$-$C_{15}$ heteroaryl group, and
wherein S has the formula 2.

7. The 1,4-bidentate ligand of claim 1, wherein the first ligand centre is in a six-membered aromatic- or heteroaromatic ring, and wherein said ring comprises a substantially linear substituent $T^2$ meta to the first ligand centre,
wherein $T^2$ has the formula (1) and may be the same or different from $T^1$, and wherein $T^2$ is attached to the ring by $X^2$, wherein $X^2$ is a bond, a methylene group, a substituted methylene group, an oxygen atom or a sulphur atom, and
wherein $T^2$ is meta to the first ligand centre.

8. The 1,4-bidentate ligand of claim 1, wherein the first ligand centre is a $sp^2$ hybridised carbon and forms part of a 6-membered aromatic ring; and/or
wherein the second ligand centre forms part of a 6-membered aromatic ring.

9. The 1,4-bidentate ligand of claim 1, wherein the complex has an octahedral bis-heteroleptic or tris-heteroleptic structure, or a square planar bis-homoleptic or bis-heteroleptic structure.

10. The ligand of claim 1 comprising a complex, wherein the complex has two 1,4-bidentate ligands each comprising the same $T^1$ and, where present, $T^2$ substituents.

11. The 1,4-bidentate ligand of claim 1 wherein the 1,4-bidentate ligand is coordinated to iridium (III), platinum (II), osmium (II) or ruthenium (II) in a complex, in a composition with a nematic liquid crystalline material; wherein the nematic liquid crystalline material is cross-linkable.

12. The 1,4-bidentate ligand of claim 11 wherein the complex constitutes from 1 to 50 wt % of the composition.

13. A device comprising one or more charge transport layers and/or emissive layers comprising a network polymer formed by exposure of the 1,4-bidentate ligand of claim 1 to radiation.

14. The device according to claim 13, wherein the device is an OLED device, a photovoltaic device or a thin film transistor (TFT) device.

15. The device according to claim 13, wherein the network polymer is provided in a hole transporting layer or an electron transporting layer provided directly adjacent an electron transporting layer or a hole transporting layer respectively.

16. A device according to claim 13 which is an OLED device having a light emitting emissive layer and wherein the network polymer forms a uniformly aligned liquid crystalline structure within the emissive layer whereby the light emitting emissive layer emits linearly polarised light.

17. A method for forming a device comprising one or more charge transport layers and/or emissive layers comprising a network polymer, the method comprising:
providing a layer comprising the 1,4-bidentate ligand of claim 1;
selectively irradiating the layer with irradiation to form a network polymer; and
washing away any non-irradiated and unpolymerized ligand.

18. The method according to claim 17, further comprising providing a further layer comprising a 1,4-bidentate ligand comprising first and second ligand centres,
wherein the first ligand centre is an $sp^2$-hybridised carbon or a nitrogen atom;
wherein the second ligand centre is a nitrogen atom in a five- or six-membered aromatic or hetero-aromatic ring, said ring having a substantially linear substituent $T^1$ meta or para to the nitrogen atom;

wherein $T^1$ has the formula (1):

$$-Ar^1{}_a-Y^1{}_b-Ar^2-[Y^2{}_c-Ar^2]_d-S-B \qquad (1)$$

and wherein $T^1$ is attached to the ring by $X^1$, wherein $X^1$ is a bond, a methylene group, a substituted methylene group, an oxygen atom or a sulphur atom,
wherein each $Ar^1$ and $Ar^2$ are independently selected from the group of $C_6$ to $C_{20}$ aromatic and $C_4$ to $C_{20}$ heteroaromatic groups,
wherein $Y^1$ and each $Y^2$ is independently an optionally substituted $C_2$ or acetonitrile trans double-bond linking moiety,
wherein a is 0, 1, 2 or 3,
wherein b is 0, 1 or 2,
wherein each c is independently 0, 1 or 2,
wherein d is 0, 1 ,2, 3 or 4,
S is a flexible spacer, and
B represents a moiety having one or more cross-linkable functionalities;
selectively irradiating the further layer with irradiation to form a network polymer; and
washing away any non-irradiated and unpolymerized ligand from the further layer.

19. The method of claim 17 wherein providing the layer comprises providing a layer of a complex or composition comprising the ligand.

20. The 1,4-bidentate ligand of claim 8, wherein the 6-membered aromatic ring is pyridine.

* * * * *